US009730993B2

(12) United States Patent
Leysath et al.

(10) Patent No.: US 9,730,993 B2
(45) Date of Patent: Aug. 15, 2017

(54) ENGINEERED ANTHRAX LETHAL TOXIN FOR TARGETED DELIVERY

(71) Applicant: The United States of America as Represented by the Secretary of the Department of Health and Human Services, Washington, DC (US)

(72) Inventors: Clinton Edward Leysath, College Station, TX (US); Stephen H Leppla, Rockville, MD (US); Damilola Daniel Phillips, Rockville, MD (US)

(73) Assignee: The United States of America, as Represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/423,408

(22) PCT Filed: Aug. 22, 2013

(86) PCT No.: PCT/US2013/056205
§ 371 (c)(1),
(2) Date: Feb. 23, 2015

(87) PCT Pub. No.: WO2014/031861
PCT Pub. Date: Feb. 27, 2014

(65) Prior Publication Data
US 2015/0224184 A1   Aug. 13, 2015

Related U.S. Application Data

(60) Provisional application No. 61/692,143, filed on Aug. 22, 2012.

(51) Int. Cl.
*A61K 39/07* (2006.01)
*A61K 47/48* (2006.01)
*C07K 14/32* (2006.01)
*A61K 39/104* (2006.01)

(52) U.S. Cl.
CPC ............ *A61K 39/07* (2013.01); *A61K 39/104* (2013.01); *A61K 47/48346* (2013.01); *C07K 14/32* (2013.01)

(58) Field of Classification Search
None
See application file for complete search history.

(56) References Cited

FOREIGN PATENT DOCUMENTS

| WO | 2005/090393 A2 | 9/2005 |
|---|---|---|
| WO | 2005/090393 A3 | 9/2005 |

OTHER PUBLICATIONS

International Search Report and Written Opinion dated Jun. 2, 2014 of International Patent Application No. PCT/US2013/056205, 15 pages.
Liu et al., "Tumor cell-selective cytotoxicity of matrix metalloproteinase-activated anthrax toxin", *Cancer Research*, vol. 60, No. 21, pp. 6061-6067 (2000).
Liu et al., "Targeting of tumor cells by cell surface urokinase plasminogen activator-dependent anthrax toxin", *Journal of Biological Chemistry*, vol. 276, No. 21, pp. 17976-17984 (2001).
Liu et al., "Intermolecular complementation achieves high-specificity tumor targeting by anthrax toxin", *Nature Biotechnology*, vol. 23, No. 6, pp. 725-730 (2005).
Mogridge et al., "The lethal and edema factors of anthrax toxin bind only to liogomeric forms of the protective antigen", *Proceedings of the National Academy of Sciences*, vol. 99, No. 10, pp. 7045-7048 (2002).
Phillips et al., "Engineering Anthrax Toxin Variants That Exclusively Form Octamers and Their Application to Targeting Tumors", *Journal of Biological Chemistry*, vol. 288, No. 13, pp. 9058-9065 (2013).

*Primary Examiner* — Patricia Duffy
(74) *Attorney, Agent, or Firm* — Kilpatrick Townsend & Stockton LLP

(57) ABSTRACT

The present invention provides methods and systems for targeted delivery of a compound to a target cell that overexpresses two different proteinases. Specifically, two different modified protective antigen proteins, each comprising a cleavage site recognized by a distinct proteinase in place of the native proteinase cleavage site recognized by furin, are administered in combination with a compound that contains a protective antigen binding site. Upon cleavage by the two proteinases the two modified protective antigen proteins form a hetero-oligomer, allowing the compound to bind to the hetero-oligomer and subsequently to be translocated into the target cell.

34 Claims, 13 Drawing Sheets
(1 of 13 Drawing Sheet(s) Filed in Color)

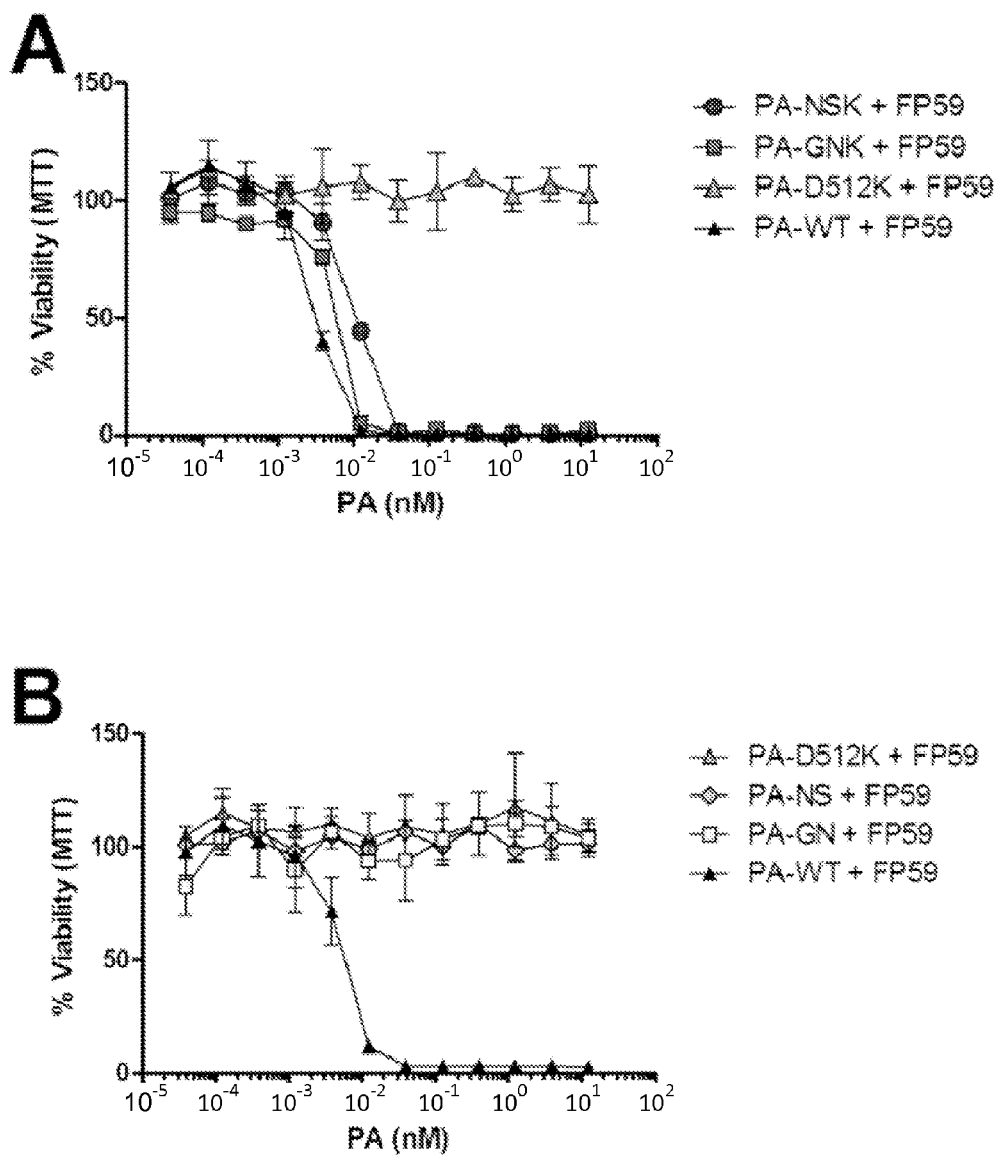
FIGS. 3A-B

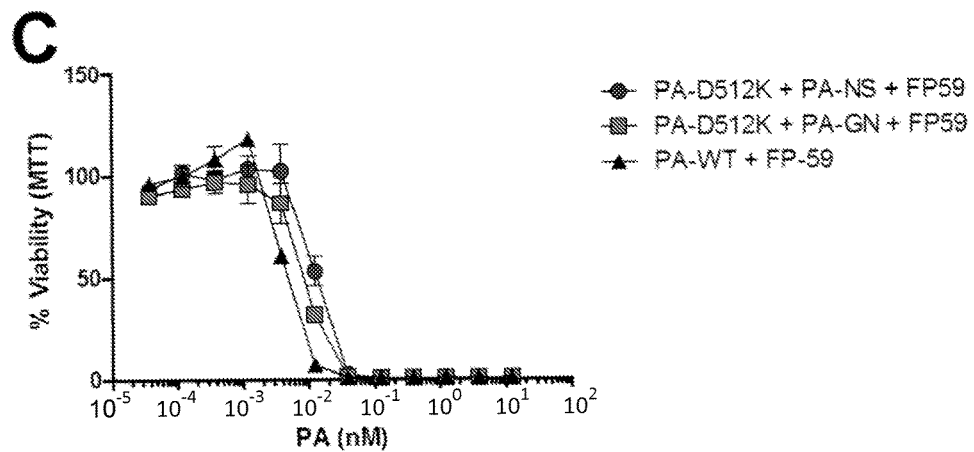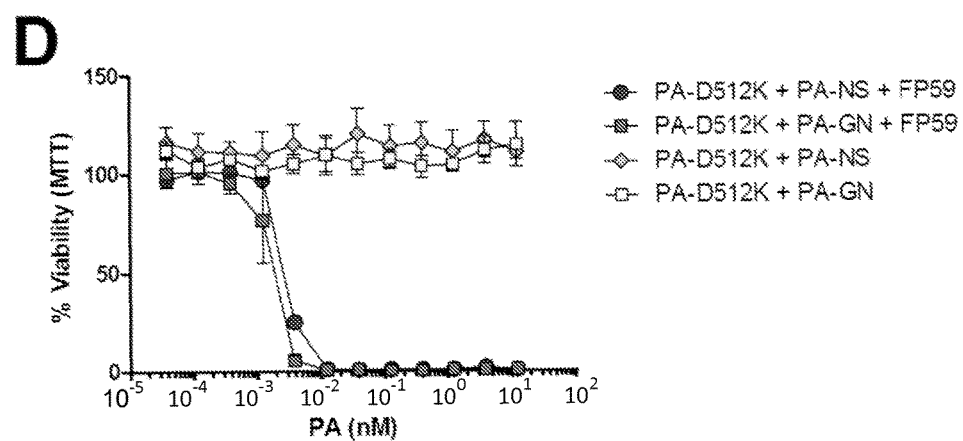
FIGS. 3C-D

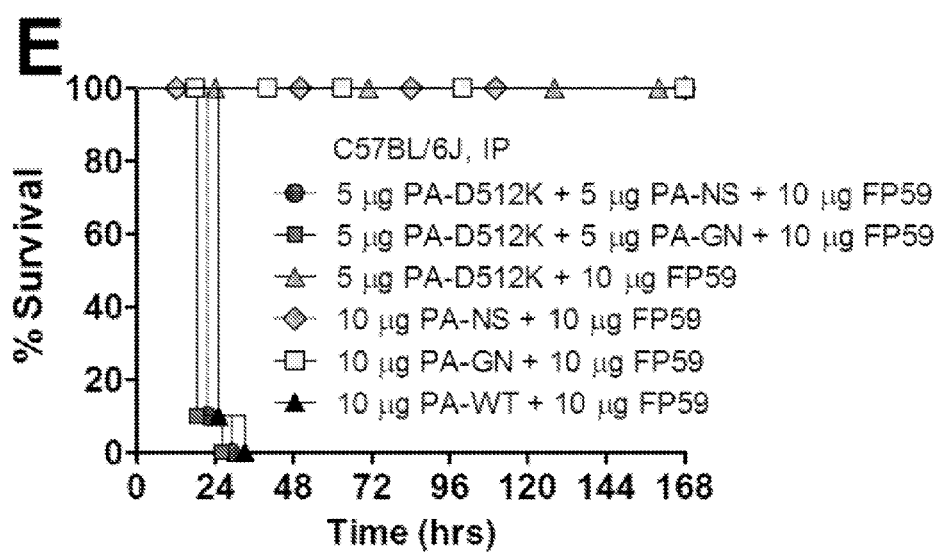
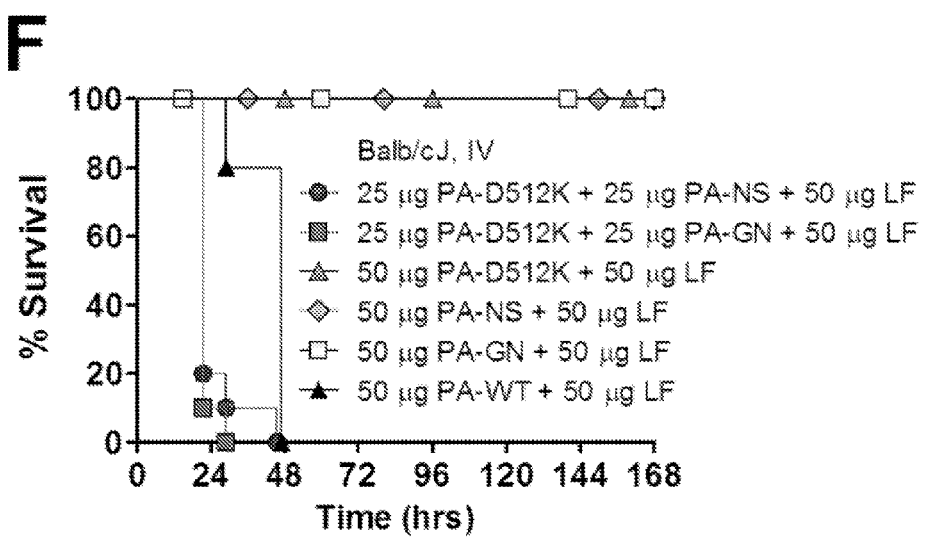
FIGS. 3E-F

A

*c(s)* ($A_{250}$/S) vs $s_{20,w}$(S)

B

| PA-WT | PA-WT + LF | PA-NS + PA-D512K + LF | PA-GN + PA-D512K + LF |

ENGINEERED ANTHRAX LETHAL TOXIN FOR TARGETED DELIVERY

CROSS-REFERENCE TO RELATED APPLICATIONS

This application is a US National Phase of PCT Application No. PCT/US2013/056205, filed Aug. 22, 2013, which claims priority to U.S. Provisional Patent Application No. 61/692,143, filed Aug. 22, 2012, the contents of which are herein incorporated by reference in the entirety.

REFERENCE TO SEQUENCE LISTING

This application includes a Sequence Listing as a text file named "77867-936677-SEQLIST.txt" created Feb. 20, 2015, and containing 4,317 bytes. The material contained in this text file is incorporated by reference in its entirety for all purposes.

BACKGROUND OF THE INVENTION

Anthrax toxin is a three-part toxin secreted by *Bacillus anthracis* consisting of protective antigen (PA, 83 kDa), lethal factor (LF, 90 kDa) and edema factor (EF, 89 kDa) (Smith et al., *J. Gen. Microbiol.*, 29:517-521 (1962); Leppla, *Sourcebook of bacterial protein toxins*, p. 277-302 (1991); Leppla, *Handb. Nat. Toxins*, 8:543-572 (1995)), which are individually non-toxic. The mechanism by which individual toxin components interact to cause toxicity is reviewed in Leppla, *Handb. Nat. Toxins*, 8:543-572 (1995). Protective antigen, the central component of the Anthrax toxin system, is cleaved at the sequence $RKKR_{167}$ (SEQ ID NO:15) by cell surface furin or furin-like proteases (Klimpel et al., *Proc. Natl. Acad. Sci. USA*, 89:10277-10281 (1992); Molloy et al., *J. B. Chem.*, 267:16396-16402 (1992)) into two fragments: PA63, a 63 kDa C-terminal fragment, which is capable of forming oligomers of multiple PA63 units; and PA20, a 20 kDa N-terminal fragment, which is released and plays no further part in the Anthrax toxin scheme (Klimpel et al., *Mol. Microbiol.*, 13:1094-1100 (1994)). Dissociation of PA20 allows PA63 to form heptamers (Milne et al., *J. Biol. Chem.*, 269:20607-20612 (1994); Benson et al., *Biochemistry*, 37:3941-3948 (1998)) and octamers (Kintzer et al., *J. Mol. Biol.*, 392:614-629 (2009)) that bind LF or EF (Leppla et al., *Bacterial protein toxins*, p. 111-112 (1988)), and the resulting hetero-oligomeric complex is internalized by endocytosis (Gordon et al., *Infect. Immun.*, 56:1066-1069 (1988)).

Recognizing the importance of protective antigen activation by proteolytic cleavage, researchers have in the past decade or so engineered several modified versions of protective antigen mutants to replace the native furin cleavage site with the recognition site of anther pre-selected proteinase in order to specifically target cells that overexpress the proteinase for delivery of an effector molecule, such as lethal factor or edema factor. For example, mutant protective antigen proteins have been made to contain cleavage site recognized by matrix metalloproteinases (MMPs) and proteases of the plasminogen activation system (such as tissue plasminogen activator (t-PA) and urokinase plasminogen activator (u-PA), see, e.g., Romer et al., *APMIS* 107:120-127 (1999)), which are typically overexpressed in tumors, such that the modified Anthrax toxin systems can be used in a tumor-specific delivery scheme. See, e.g., WO01/21656 and WO2008/076939.

Since these modified Anthrax toxin systems rely on the overexpression of just one proteinase to target a cell population, undesired side effects stemmed from non-specific cytotoxicity have been a concern. Although efforts have been made to enhance target specificity and reduce non-specific cytotoxicity (see, e.g., Liu et al., *Nature Biotech.* 23(5):725-730 (2005)), there remains a pressing need to further improve the Anthrax toxin delivery system for even higher delivery efficiency and lower side-effect toxicity. The present invention fulfills this and other related needs.

BRIEF SUMMARY OF THE INVENTION

The present inventors have successfully designed and generated a new and modified Anthrax toxin delivery system to achieve superior delivery results as indicated by increased target specificity and reduced non-specific cytotoxicity. This new system utilizes at least two differently mutated protective antigen proteins, each of which is subject to proteolytic cleavage by different proteinases. The post-cleavage products of these different protective antigen mutants then form hetero-oligomers (but not homo-oligomers), allowing the compound to be delivered to the target cell to bind to the hetero-oligomer and to be subsequently translocated into the target cell. As such, in one aspect, the present invention provides a method for targeted delivery of a compound to a cell that overexpresses two distinct proteinases. The method includes steps (a) and (b): step (a) is administering to the cell targeted for delivery (1) a first mutant protective antigen protein. This first mutant protective antigen protein contains a cleavage site recognized by the first proteinase, located at the same location within the protective antigen protein as the native furin-recognized cleavage site in the protective antigen protein to replace the native furin cleavage site. This first mutant protective antigen protein is cleavable by the first proteinase; and (2) a second mutant protective antigen protein, co-administered with the first mutant protective antigen. This second mutant protective antigen protein contains a cleavage site recognized by the second proteinase, located at the same location within the protective antigen protein as the native furin-recognized cleavage site in the protective antigen protein to replace the native furin cleavage site. This second mutant protective antigen protein is cleavable by the second proteinase. The first and second mutant protective antigen proteins each comprises an additional mutation other than the cleavage sites recognized by the first and second proteinases, respectively. Upon cleavage by the first and second proteinases, the first and second mutant protective antigen proteins release their respective N-terminal fragments, and their remaining C-terminal fragments form a hetero-oligomer but do not form a homo-oligomer. Step (b) is administering to the cell a compound intended to be delivered to the target cell. This compound includes a protective antigen binding site, allowing the compound to bind to the hetero-oligomer and to be translocated into the target cell.

In some embodiments, the first proteinase is a plasminogen activator and the second proteinase is a matrix metalloproteinase, or vice versa. For example, the plasminogen activator may be tissue plasminogen activator (t-PA) or urokinase plasminogen activator (u-PA), whereas the matrix metalloproteinase may be MMP-2 (gelatinase A), MMP-9 (gelatinase B), or membrane-type 1 MMP (MT1-MMP). The matrix metalloproteinase-recognized cleavage site sequence suitable for use in constructing the first or second mutant protective antigen protein includes GPLGMLSQ (SEQ ID NO:9) or GPLGLWAQ (SEQ ID NO:10), whereas the plasminogen activator-recognized cleavage site sequence suitable for use in the first or second mutant protective antigen protein include PCPGRVVGG (SEQ ID NO:11), PGSGRSA (SEQ ID NO:12), PGSGKSA (SEQ ID NO:13), or PQRGRSA (SEQ ID NO:14). Any one of the matrix metalloproteinase cleavage sites may be used with any one of the plasminogen activator cleavage sites to construct the first and second mutant protective antigen proteins.

In some embodiments, the first or the second proteinase is furin. In some cases, the native protective antigen furin-recognized cleavage site RKKR (SEQ ID NO:15) is unchanged in the first or second mutant protective antigen protein, whereas in other cases the native protective antigen furin-recognized cleavage site in the first or second mutant protective antigen protein that is cleavable by furin is replaced with RAAR (SEQ ID NO:16) or RARAAR (SEQ ID NO:17).

In some embodiments, the intended target cell to receive the compound is a cancer cell, which may be within a human body, for example, as a part of a human cancer. When the compound is delivered to target cells that are a part of human cancer within a patient's body, the first and second mutant protective antigen proteins and the compound may be administered systemically or locally to the human, e.g., by intravenous, oral, topical, intraperitoneal, intravesical, intranasal, or intrathecal administration In some embodiments, the compound being delivered to the target cell is a lethal factor polypeptide or a molecule comprising at least a portion of the native lethal factor protein. For example, the lethal factor polypeptide is the native lethal factor protein, or the 1-254 segment of the native lethal factor protein. In some cases, the lethal factor polypeptide is the native lethal factor or a portion thereof fused to a heterologous molecule, which may be any chemical or biological nature, such as a toxin (e.g., shiga toxin, A chain of diphtheria toxin, or *Pseudomonas* exotoxin A, a detectable moiety, or a nucleic acid. Frequently, the heterologous molecule is covalently linked to the native lethal factor or a portion thereof. In the case of the heterologous molecule being another protein or polypeptide, the compound to be delivered is a recombinant polypeptide. One example of such a compound is FP59, a recombinant polypeptide of the first 254 amino acids of the N-terminal portion of the native lethal factor protein fused with the catalytic domain of *Pseudomonas* exotoxin A.

In some embodiments, the hetero-oligomer formed by the first and second mutant protective antigen proteins following cleavage by their respective proteinases includes equal numbers of the first and second mutant protective antigen proteins, for example, the hetero-oligomer may be an octamer consisting of four of each of the first and second mutant protective antigen proteins.

In some embodiments, the additional mutation in one of the first and second mutant protective antigen proteins is a mutation at residue 512, and the additional mutation in the other of the first and second mutant protective antigen proteins is a mutation at residue 245 and a mutation at residue 252. In one example, residue 512 is substituted by Lys, and residue 245 is substituted by Gly and residue 252 is substituted by Asn. In another example, residue 512 is substituted by Lys, and residue 245 is substituted by Asn and residue 252 is substituted by Ser. As in either example, the first proteinase may be u-PA and the second proteinase may be MMP-2, and the compound may be the native lethal factor protein.

In another aspect, the present invention provides a kit for targeted delivery of a compound to a target cell, which overexpresses two different proteinases. The kit includes the following components: (1) a first mutant protective antigen protein; (2) a second mutant protective antigen protein; and (3) a compound that is intended to be delivered into the target cell. The first mutant protective antigen protein contains a cleavage site recognized by the first proteinase, located at the same location within the protective antigen protein as the native furin-recognized cleavage site in the protective antigen protein in place of the native furin cleavage site, making the first mutant protective antigen protein cleavable by the first proteinase. The second mutant protective antigen protein contains a cleavage site recognized by the second proteinase, located at the same location within the protective antigen protein as the native furin-recognized cleavage site in the protective antigen protein in place of the native furin cleavage site, making the second mutant protective antigen protein cleavable by the second proteinase. The first and second mutant protective antigen proteins each contains an additional mutation other than the cleavage sites recognized by the first and second proteinases, respectively. Upon cleavage by the first and second proteinases, the first and second mutant protective antigen proteins release their respective N-terminal fragments, and their remaining C-terminal fragments form a hetero-oligomer but do not form a homo-oligomer. The compound to be delivered to the target cell contains a protective antigen binding site, which allows the compound to bind to the hetero-oligomer and to be translocated into the target cell.

In some embodiments, the first proteinase is a plasminogen activator and the second proteinase is a matrix metalloproteinase, or vice versa. For example, the plasminogen activator may be tissue plasminogen activator (t-PA) or urokinase plasminogen activator (u-PA), whereas the matrix metalloproteinase may be MMP-2 (gelatinase A), MMP-9 (gelatinase B), or membrane-type 1 MMP (MT1-MMP). The matrix metalloproteinase-recognized cleavage site sequence suitable for use in constructing the first or second mutant protective antigen protein includes GPLGMLSQ (SEQ ID NO:9) or GPLGLWAQ (SEQ ID NO:10), whereas the plasminogen activator-recognized cleavage site sequence suitable for use in the first or second mutant protective antigen protein include PCPGRVVGG (SEQ ID NO:11), PGSGRSA (SEQ ID NO:12), PGSGKSA (SEQ ID NO:13), or PQRGRSA (SEQ ID NO:14). Any one of the matrix metalloproteinase cleavage sites may be used with any one of the plasminogen activator cleavage sites to construct the first and second mutant protective antigen proteins to produce the claimed kit.

In some embodiments, the first or the second proteinase is furin. In some cases, the native protective antigen furin-recognized cleavage site RKKR (SEQ ID NO:15) is unchanged in the first or second mutant protective antigen protein, whereas in other cases the native protective antigen furin-recognized cleavage site in the first or second mutant protective antigen protein that is cleavable by furin is replaced with RAAR (SEQ ID NO:16) or RARAAR (SEQ ID NO:17).

In some embodiments, the intended target cell to receive the compound is a cancer cell, which may be within a human body, for example, as a part of a human cancer. When the compound is delivered to target cells that are a part of human cancer within a patient's body, the first and second mutant protective antigen proteins and the compound may be administered systemically or locally to the human. As such, the first and second mutant protective antigen proteins and the compound may be formulated in a manner suitable for administration such as by intravenous, oral, topical, intraperitoneal, intravesical, intranasal, or intrathecal administration.

In some embodiments, the compound being delivered to the target cell is a lethal factor polypeptide or a molecule comprising at least a portion of the native lethal factor protein. For example, the lethal factor polypeptide is the native lethal factor protein, or the 1-254 segment of the native lethal factor protein. In some cases, the lethal factor polypeptide is the native lethal factor or a portion thereof fused to a heterologous molecule, which may be any chemical or biological nature, such as a toxin (e.g., shiga toxin, A chain of diphtheria toxin, or *Pseudomonas* exotoxin A, a detectable moiety, or a nucleic acid. Frequently, the heterologous molecule is covalently linked to the native lethal factor or a portion thereof. In the case of the heterologous molecule being another protein or polypeptide, the compound to be delivered is a recombinant polypeptide. One example of such a compound is FP59, a recombinant polypeptide of the N-terminal 1-254 segment of the native lethal factor protein fused with the catalytic domain of *Pseudomonas* exotoxin A.

In some embodiments, the first and second mutant protective antigen proteins following cleavage by their respective proteinases form a hetero-oligomer that includes equal numbers of the first and second mutant protective antigen proteins, for example, the hetero-oligomer may be an octamer consisting of four of each of the first and second mutant protective antigen proteins.

In some embodiments, the additional mutation in one of the first and second mutant protective antigen proteins is a mutation at residue 512, and the additional mutation in the other of the first and second mutant protective antigen proteins is a mutation at residue 245 and a mutation at residue 252. In one example, residue 512 is substituted by Lys, and residue 245 is substituted by Gly and residue 252 is substituted by Asn. In another example, residue 512 is substituted by Lys, and residue 245 is substituted by Asn and residue 252 is substituted by Ser. As in either example, the first proteinase may be u-PA and the second proteinase may be MMP-2, and the compound may be the native lethal factor protein.

In yet another aspect, the present invention provides a method for producing new protective antigen mutants, which, upon proteolytic cleavage, form hetero-oligomers that are functional to operate in an anthrax toxin targeted delivery system described herein. This method includes these stages: first, a primary mutant protective antigen protein comprising a primary mutation, e.g., at least one mutation in the complementary binding surface of the protective antigen (within residues 476 to 610, preferably residues 483 to 602, of the native protective antigen protein) is generated and confirmed to not form homo-oligomers after proteinase cleavage and release of the N-terminal fragment. General methods in recombinant technology can be employed to, for instance, produce a library of random mutants of protective antigen protein with a primary mutation. This process includes the generation of both polynucleotide coding sequences for the mutants and the recombinant production of the mutant proteins. The random mutants are then tested, and individual mutants unable to form homo-oligomer are identified, their nucleotide sequence and amino acid sequence determined. Such mutants each can serve as the primary mutant for further use in this method. Second, another library of random mutant protective antigen proteins is generated, each member comprising the primary mutation and a second, randomly generated mutation located within the complementary binding face of the protective antigen protein (within residues 190 to 475, preferably residues 193 to 470, of the native protective antigen protein). Each one of such randomly generated mutations may include one, two, three, or even more amino acids of the native protective antigen protein that have been mutated. Third, each of the random mutants is screened for its ability to form oligomer following proteolytic cleavage of the respective N-terminal fragment. General methods known in molecular biology can be used to generate both the polynucleotide coding sequences and the recombinant proteins of these random mutants. Methods such as electron microscopy and image analysis as described in this application and in other publications including Kintzer et al., *J. Mol. Biol.* 392:614-629 (2009) are useful for observing oligomer formation. Any one or one set of the second mutations found in a random mutant that restores formation of functional protective antigen oligomers (i.e., capable of translocating into a target cell a protective antigen binding molecule such as the native lethal factor protein), when combined with the primary mutant, is referred to as a complementary mutation. For example, the D512K mutation described in this application is a primary mutation, whereas the K245G/R252N (GN) and K245N/R252S (NS) mutations are two complementary mutations. Fourth, after one or more complementary mutations are identified, a first mutant protective antigen protein is produced to contain only the primary mutation, and a second mutant protective antigen protein is produced to contain only one complementary mutation. The ability of the first and second mutant protective antigen proteins to form hetero-oligomers but form no homo-oligomers is then verified using the assay systems described in this application and in the art. Additional, e.g., a third, fourth, or fifth mutant protective antigen protein may be generated to contain the third, fourth, or fifth complementary mutation identified by the same process described above. As used in this application, the usage of the "first," "second," "third," etc. mutants is for easy reference only. These terms are used interchangeably among the mutants and do not inherently carry any identifying features of these mutants from one to another. For each of these mutant protective antigen proteins, the ability to form hetero-oligomer with one or more other mutant protective antigen protein(s) but not form homo-oligomers can be verified using the same electronic microscopy and imaging methods as mentioned above. Each of these mutant protective antigen proteins may contain the native furin-cleavage site, modified furin-cleavage site, or another proteinase cleavage site such as one recognized by a matrix metalloproteinase or plasminogen activator. While each of the mutant protective antigen proteins may contain any one of the proteinase cleavage sites, cleavage sites recognized by at least two different proteinases are included among the at least two mutant protective antigen proteins to be used in the same delivery system in order to ensure a high level of target cell specificity.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3: In vitro and in vivo toxicity studies of PA variants. In vitro toxicity studies were performed by exposing 50,000 RAW264.7 cells/well to varying concentrations of PA with 1.8 nM FP59 (a fusion protein composed of the N-terminal PA-binding domain of LF linked to the catalytic domain of *Pseudomonas* exotoxin A) for 24 h. Viability was then measured by MTT assay. Experiments were performed in triplicate, and error bars denote standard deviations. Concentrations are for the total PA concentration if two variants are mixed. (A) Toxicities were assessed for PA variants isolated from the library. (B) Toxicities of complementary PA variants were determined. (C) Combinations of complementary PA variants were compared to wild type PA. (D) Complementary PA variants were administered in the presence or absence of FP59. (E, F) For in vivo tests, PA variants were administered intraperitoneally or intravenously either individually or in combinations to C57BL/6J (E) or Balb/cJ (F) mice (n=10/group) together with FP59 or LF, and animal survival monitored. Mouse survival times following all PA wild type and combination treatments were significantly different from single variant controls (p<0.0001) using a log rank test.

FIG. 5: Biophysical characterization of oligomeric PA variants. (A) Characterization of PA and LF complexes by sedimentation velocity. Absorbance c(s) distributions obtained in SEDFIT for wild type PA oligomer at 1.32 mg/mL (black), wild type PA+LF 2.36 mg/mL (green), PA-D512K+PA-GN+LF at 0.74 mg/mL (blue), and PA-D512K+PA-NS+LF at 0.63 mg/mL (red). Each sample showed the presence of a predominant species. Similar profiles were observed using the interference optical system. (B) EM images of heptameric and octameric PA species. The top row shows representative unprocessed cryo-EM images from the samples indicated. The scale bar=20 nm and applies to this row only. The middle row shows the classes that resulted from the reference-free alignment, and the final row is a compressed overlay of the respective classes for each sample. Scale bars for middle and bottom rows=5 nm.

Figure 8:
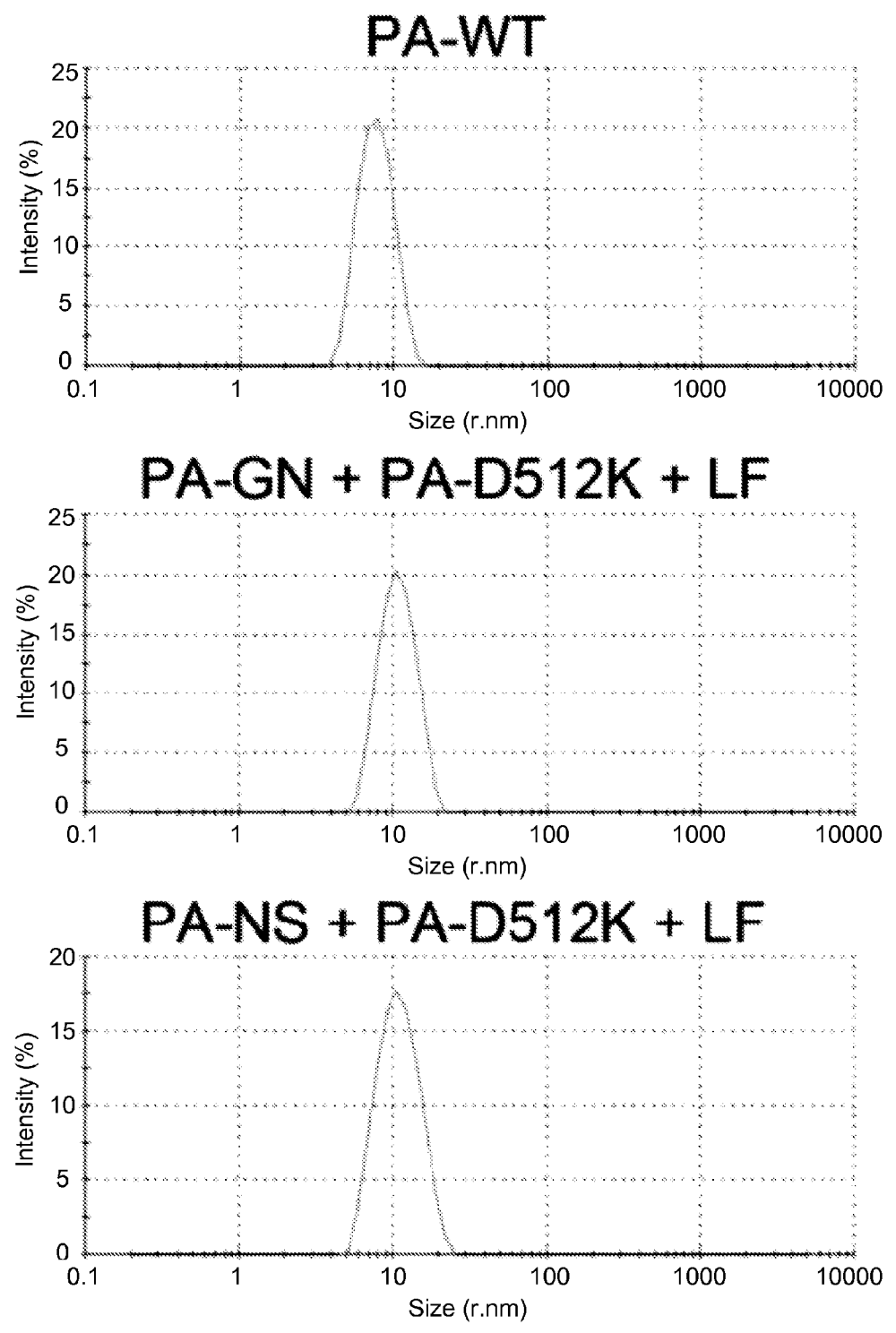

FIG. 8: Dynamic light scattering measurements of PA oligomers. Purified complexes formed by PA-WT, PA-GN+ PA-D512K+LF, and PA-NS+PA-D512K+LF were analyzed for homogeneity. Each sample produced a single peak corresponding to a radius of 7.4, 10.3, and 10.3 nm, respectively.

DETAILED DESCRIPTION OF THE INVENTION

I. Introduction

Figure 1:
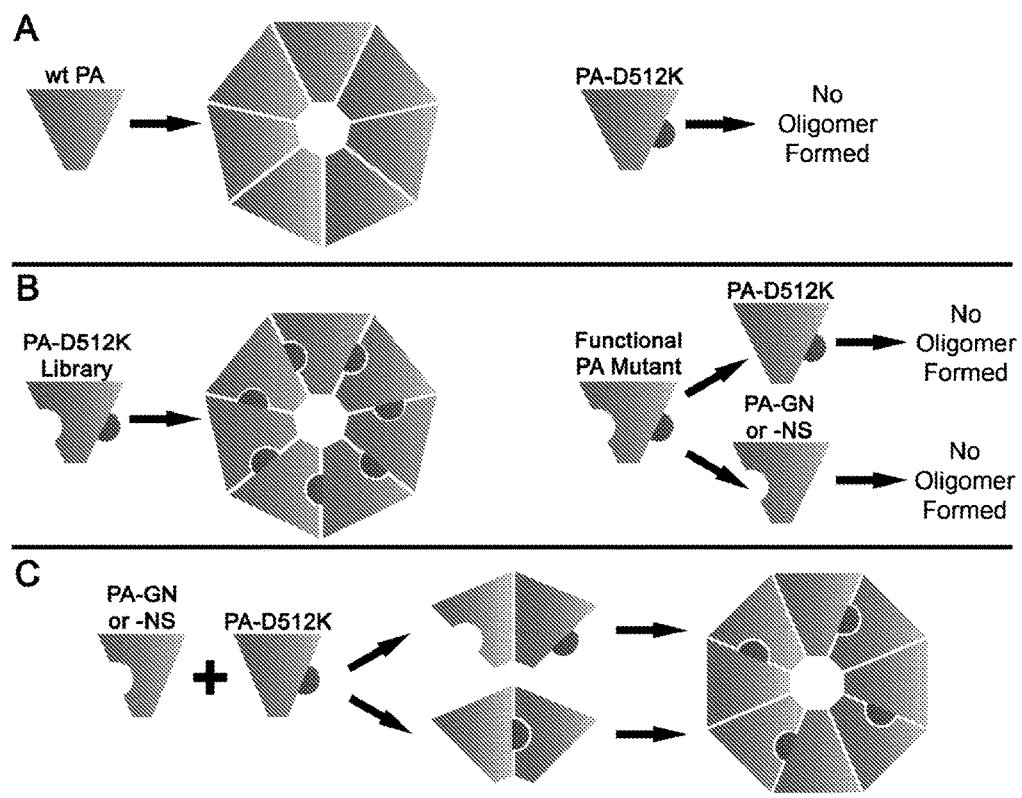
FIG. 1: Scheme for discovery of PA mutants that form selective octamers. (A) Wild type PA oligomerizes to predominantly form heptamers, while point mutant PA-13512K is oligomerization deficient. (B) A library was created using PA-D512K by introducing diversity at residues on the complementary binding surface to the face of PA that contains the D512K mutation and screened for variants that possessed gain of function mutations. After successful isolation of the functional PA variants, separation of the mutations from D512K was necessary to confirm that the substitutions were individually loss of function mutations. (C) Combining both complementary PA variants allows formation of oligomers using two unique interfaces (wild type and engineered). This allows the formation of only even-numbered oligomers, in which octamers predominate.
Figure 2:
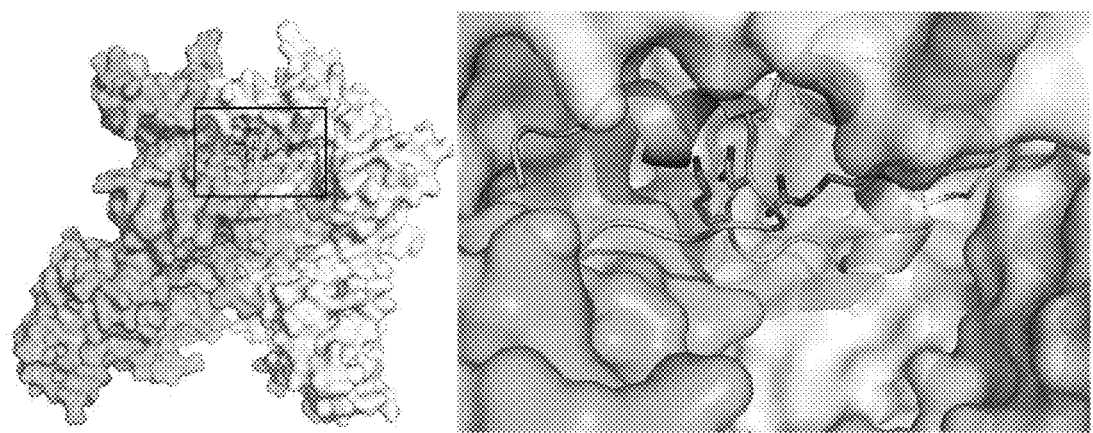
FIG. 2: Locations of mutated residues at the interface of two PA63 molecules. An illustration of two adjacent PA63 monomers (one in green, the other in white) was made using the crystal structure of the PA pre-pore (1TZO) (Lacy et al., 2004, *Pro. Natl. Acad. Sci.* 101:13147-13151). Each PA molecule is rendered as a surface, while the green loop containing residue D512 as well as the white loop containing residues K245 and R252 are rendered in cartoon form for the sake of clarity. Residue D512 is colored light blue, while residues K245 and 8252 are colored dark blue.
Figure 4:
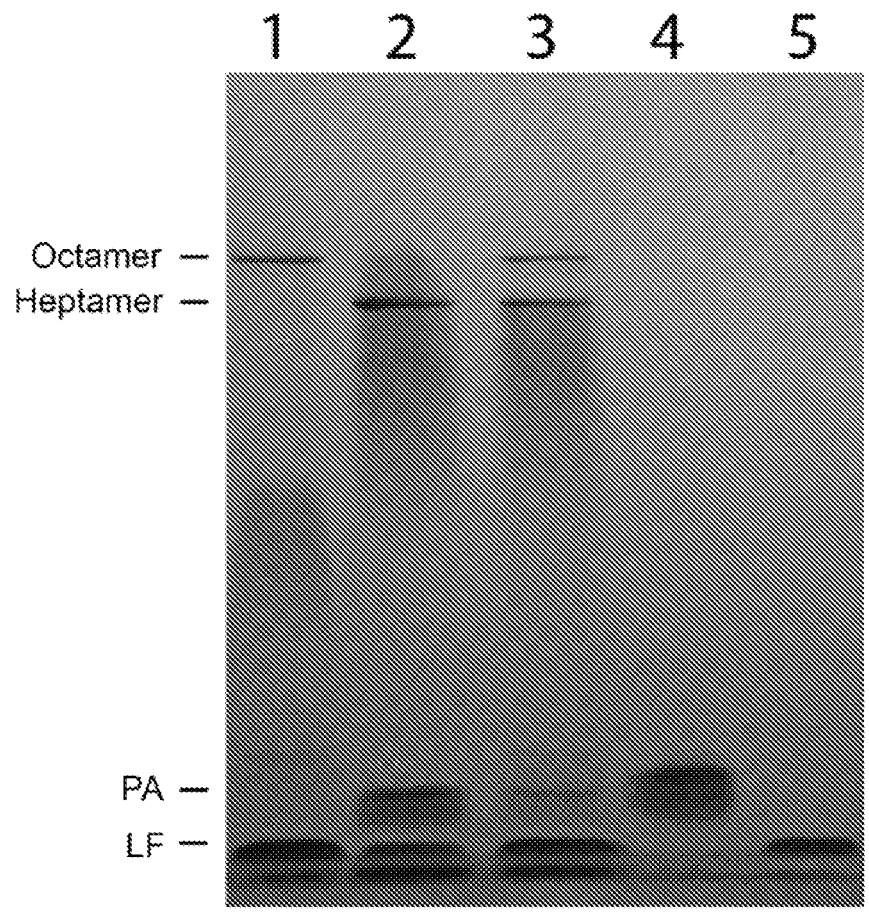
FIG. 4: Native gel electrophoresis of PA oligomers. Electrophoresis of protein complexes were performed as described in materials and methods (Singh et al. 1999, *Infec. Immu.* 67, 1853-1859). Samples are (1) cleaved PA-GN+ cleaved PA-D512K+LF, (2) cleaved wild type PA+LF, (3) samples 1 and 2 mixed immediately before electrophoresis, (4) uncleaved wild type PA, and (5) LF.
Figure 6A:
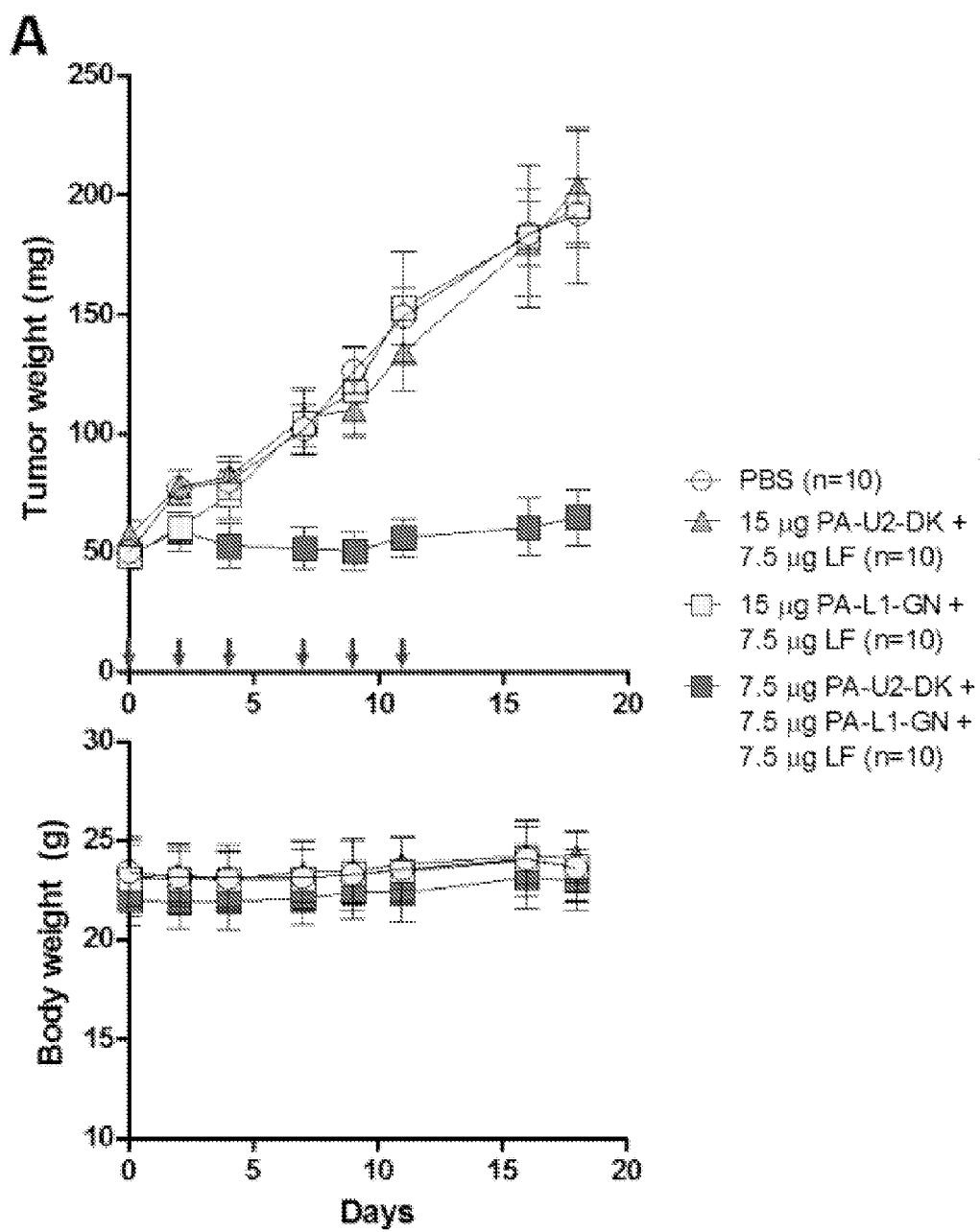
FIG. 6: Tumor targeting by complementary PA variants. (A) Nude mice (n=10/group) having 50-mg tumors composed of A549 cells (resulting from injection of 1×10⁶ cells/animal intradermally) were injected IP on days 0, 2, 4, 7, 9, and 11 with PBS, 15 µg of PA and 7.5 µg of LF, or a combination of complementary PA variants (7.5 µg of each) and 7.5 µg of LF. Tumor weight and body weight were measured on these days. There were no animal deaths observed at this dose. Error bars denote standard deviation. (B) Nude mice (n=9 or 10 per group) with tumors composed of A549 cells (from 5×10⁶ cells/animal intradermally) were injected intraperitoneally using the same schedule as in (A) with PBS, the previously published intercomplementing system (25 µg PA-U2-R200A+25 µg PA-L1-I210A+25 µg LF), or the octameric delivery system (25 µg PA-U2-DK+25 µg PA-L1-GN+25 µg LF). Tumor weight, body weight, and survival were monitored. Error bars denote standard deviation.
Figure 6B:
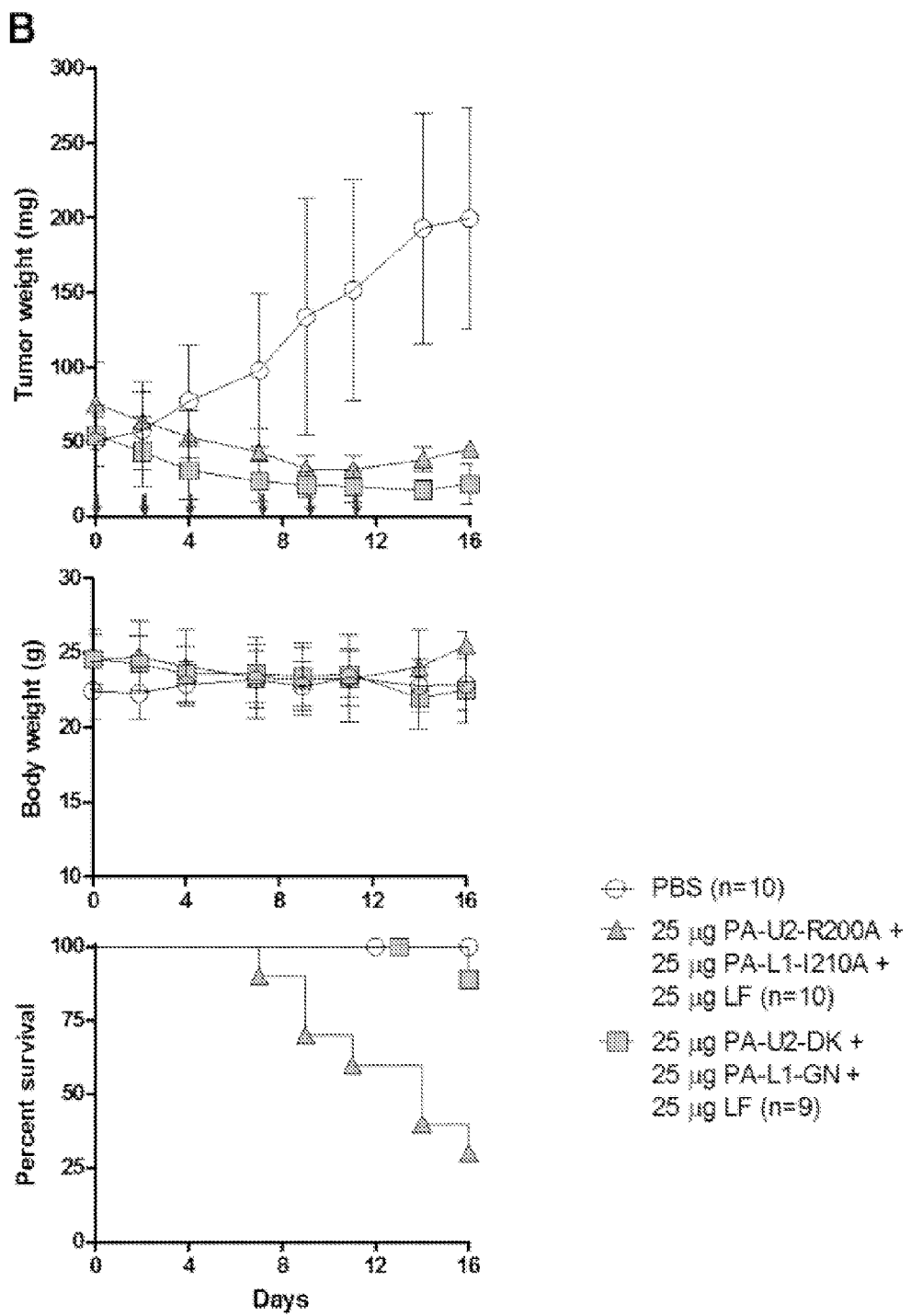
Figure 7:
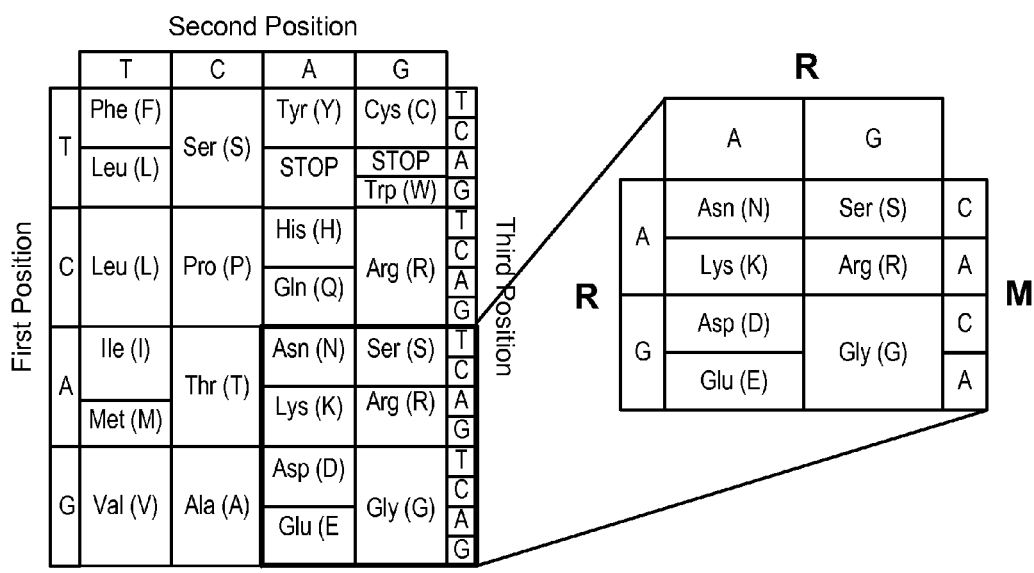
FIG. 7: Scheme for library construction. In order to maximize diversity while minimizing library size, a focused library was constructed using only ⅛ of the codon table. By utilizing the degenerate codon RRM (R=A or G, M=A or C), 7 amino acids were accessed by 8 codons containing charged amino acids lysine, arginine, aspartic acid, glutamic acid, as well as asparagine, serine, and glycine.
Figure 9:
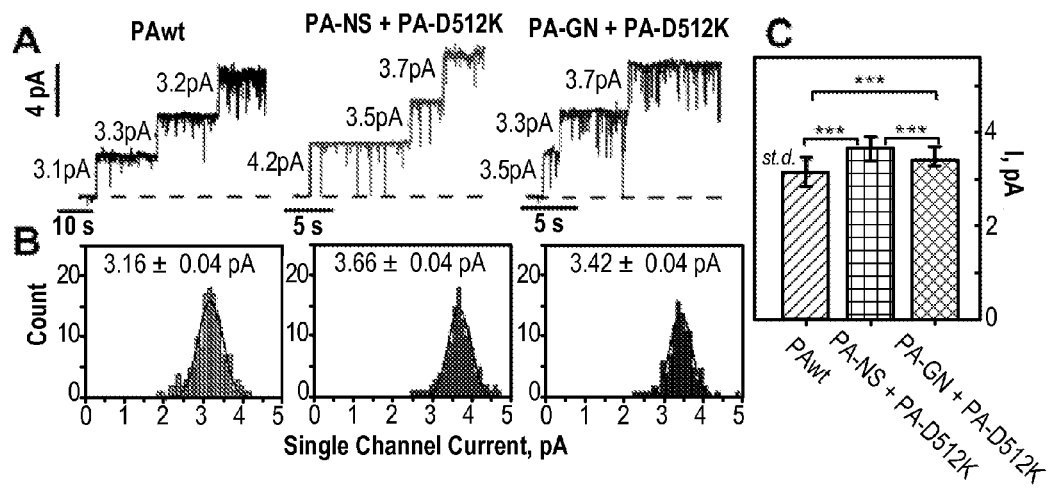
FIG. 9: Electrophysiological measurements of octameric PA variants in lipid bilayers. (A) Typical recordings of the current through the wild type PA, PA-NS+PA-D512K, and PA-GN+PA-D512K channels. The three consecutive single channel insertions are shown at a 50-ms time resolution. (B) Current histograms for the single heptameric (left) and octameric (middle and right) $PA_{63}$ channels. The peak amplitudes are given with the standard error of the mean. (C) The difference in the ion current amplitudes between the wild type PA, PA-NS+PA-D512K, and PA-GN+PA-D512K pores is statistically significant. *** is ascribed to p≤1.8× $10^{-5}$. In contrast to (B), errors represent standard deviation of the current amplitudes, where the amplitudes used for a p values calculation are equal to 3.16±0.30 pA, 3.6±0.26 pA and 3.42±0.28 pA respectively for the wild type PA, PA-NS+ PA-13512K, and PA-GN+PA-D512K pores. These values correspond to single channel conductances equal to $G_{PA\ wt}$=63±6 pS, $G_{PA-NS+PA-D512K}$=73±5 pS, and $G_{PA-GN+PA-D512K}$=68±6 pS. Measurements were performed in 0.1 M KCl, at pH 6 (5 mM MES) in DPhPC membranes and 50 mV transmembrane voltage.
Figure 10:
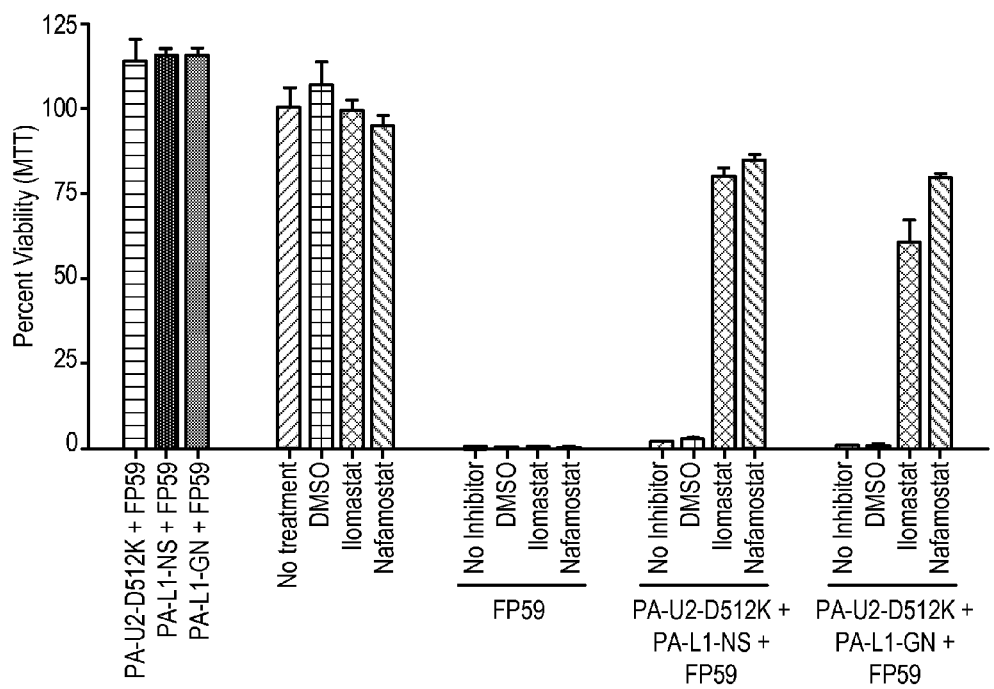
FIG. 10: Cytotoxicity of octameric toxin system requiring processing by matrix metalloproteases and urokinase plasminogen activator is attenuated by protease inhibitors. Ilomastat (25 µM), a matrix metalloprotease inhibitor, or Nafamostat mesylate (75 µM), a serine protease inhibitor (of which urokinase plasminogen activator is a family member), are sufficient to protect RAW264.7 cells from cytotoxicity associated with 1.8 nM FP59 when delivered by 3 nM total concentration of PA-U2-D512K+PA-L1-NS or PA-U2-D512K+PA-L1-GN Inhibitors were preincubated with cells for 30 min prior to addition of toxin, and 1% DMSO was used as a vehicle control. After a 6-h toxin exposure in the presence or absence of inhibitors, cells were washed with media and left overnight at 37° C. Viability was assessed using MTT at 24-h. All wells are referenced to the no treatment control. Error bars denote standard deviation.

Anthrax toxin protective antigen (PA) delivers its effector proteins (e.g., lethal factor, LF, and edema factor, EF) into the host cell cytosol through formation of an oligomeric pore, which can assume heptameric or octameric states. A necessary event preceding the formation of an oligomeric pore is the proteolytic cleavage and release of a smaller N-terminal segment of the protective antigen protein, allowing the remaining, larger C-terminal portion of the protective antigen protein to oligomerize. By screening a highly directed library of PA mutants, the present inventors identified variants that complement each other to exclusively form hetero-oligomers, such as hetero-octamers, but not homo-oligomers. These PA variants are individually non-toxic and demonstrate toxicity only when combined with their complementary partner. The inventors then engineered requirements for activation by matrix metalloproteases (MMP) and urokinase plasminogen activator (u-PA) into two of these variants. The resulting therapeutic toxin specifically targeted cells expressing both tumor cell-surface proteases, and completely stopped tumor growth in mice far below doses that were still well tolerated. This scheme for obtaining intercomplementing subunits can be employed with other oligomeric proteins, with wide potential application.

Thus, the present invention provides new and improved compositions and methods that allow targeted delivery of effector compounds to target cells overexpressing two distinct proteinases (such as a matrix metalloprotease and a plasminogen activator), achieving higher efficiency and lower non-specific cytotoxicity.

II. Definitions

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain. It may include regions preceding and following the coding region (leader and trailer) as well as intervening sequences (introns) between individual coding segments (exons).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds having a structure that is different from the general chemical structure of an amino acid, but that functions in a manner similar to a naturally occurring amino acid.

There are various known methods in the art that permit the incorporation of an unnatural amino acid derivative or analog into a polypeptide chain in a site-specific manner, see, e.g., WO 02/086075.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins*, W. H. Freeman and Co., N. Y. (1984)).

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

In the present application, amino acid residues are numbered according to their relative positions from the left most residue, which is numbered 1, in an unmodified wild-type polypeptide sequence.

As used in herein, the terms "identical" or percent "identity," in the context of describing two or more polynucleotide or amino acid sequences, refer to two or more sequences or subsequences that are the same or have a specified percentage of amino acid residues or nucleotides that are the same (for example, a mutant protective antigen protein's amino acid sequence has at least 80% identity, preferably 85%, 90%, 95% or higher identity, to a reference sequence, e.g., the wild-type protective antigen sequence, including or excluding the furin cleavage site), when compared and aligned for maximum correspondence over a comparison window, or designated region as measured using one of the following sequence comparison algorithms or by manual alignment and visual inspection. Such sequences are then said to be "substantially identical." With regard to polynucleotide sequences, this definition also refers to the complement of a test sequence. Preferably, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

Examples of algorithms that are suitable for determining percent sequence identity and sequence similarity are the BLAST and BLAST 2.0 algorithms, which are described in Altschul et al., (1990) J. Mol. Biol. 215: 403-410 and Altschul et al. (1977) Nucleic Acids Res. 25: 3389-3402, respectively. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, Proc. Natl. Acad. Sci. USA 89:10915 (1989)).

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

"Polypeptide," "peptide," and "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers.

As used herein, the terms encompass amino acid chains of any length, including full-length proteins, wherein the amino acid residues are linked by covalent peptide bonds.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

The term "effective amount," as used herein, refers to an amount that produces therapeutic effects for which a substance is administered. The effects include the prevention, correction, or inhibition of progression of the symptoms of a disease/condition and related complications to any detectable extent. The exact amount will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); and Pickar, *Dosage Calculations* (1999)).

The term "cancer" refers to human and animal cancers, including but not limited to, carcinomas, sarcomas, adenocarcinomas, lymphomas, leukemias, solid and lymphoid cancers, etc. Examples of different types of cancer include, but are not limited to, prostate cancer, renal cancer (i.e., renal cell carcinoma), bladder cancer, lung cancer, breast cancer, thyroid cancer, liver cancer (i.e., hepatocarcinoma), pleural cancer, pancreatic cancer, ovarian cancer, uterine cancer, cervical cancer, testicular cancer, colon cancer, anal cancer, pancreatic cancer, bile duct cancer, gastrointestinal carcinoid tumors, esophageal cancer, gall bladder cancer, rectal cancer, appendix cancer, small intestine cancer, stomach (gastric) cancer, cancer of the central nervous system, skin cancer, choriocarcinoma; head and neck cancer, blood cancer, osteogenic sarcoma, fibrosarcoma, neuroblastoma, glioma, melanoma, B-cell lymphoma, non-Hodgkin's lymphoma, Burkitt's lymphoma, Small Cell lymphoma, Large Cell lymphoma, monocytic leukemia, myelogenous leukemia, acute lymphocytic leukemia, acute myelocytic leukemia, and multiple myeloma.

The terms "overexpress," "overexpression," and "overexpressed" interchangeably refer to a gene that is transcribed or translated at a detectably greater level, frequently in the context of a cancer cell or a stimulated endothelial cell, in comparison to a normal cell or non-stimulated or quiescent endothelial cell. In the present invention, overexpression can therefore refer to both overexpression of MMP or plasminogen activator or plasminogen activator receptor protein and RNA, as well as local overexpression due to altered protein trafficking patterns and/or augmented functional activity. Overexpression can result, e.g., from selective pressure in culture media, transformation, activation of endogenous genes, or by addition of exogenous genes. Overexpression can be detected using conventional techniques for detecting protein (e.g., ELISA, Western blotting, immunofluorescence, immunohistochemistry, immunoassays, cytotoxicity assays, growth inhibition assays, enzyme assays, gelatin zymography, etc.) or mRNA (e.g., RT-PCR, PCR, hybridization, etc.). One skilled in the art will know of other techniques suitable for detecting overexpression of MMP or plasminogen activator or plasminogen activator receptor protein or mRNA. For example, cancerous cells or stimulated endothelial cells can overexpress such proteins or RNAs at a level of at least about 5%, 10%, 15%, 20%, 25%, 30%, 35%, 40%, 45%, 50%, 55%, 60%, 65%, 70%, 75%, 80%, 85%, 90%, or 95% in comparison to corresponding normal, non-cancerous cells, or non-stimulated or quiescent endothelial cells. Cancerous cells or stimulated endothelial cells can also have at least about a 1-fold, 2-fold, 3-fold, 4-fold, 5-fold, 6-fold, or 7-fold higher level of MMP or plasminogen activator system protein transcription or translation in comparison to normal, non-cancerous cells, or non-stimulated or quiescent endothelial cells. In some cells, the expression of these proteins is very low or undetectable. As such, expression includes no expression, i.e., expression that is undetectable or insignificant.

Examples of cells overexpressing a MMP include the tumor cell lines, fibrosarcoma HT1080, melanoma A2058, and breast cancer MDA-MB-23 1. An example of a cell which does not overexpress a MMP is the non-tumor cell line Vero. An example of a cell that overexpresses a plasminogen activator receptor are the uPAR overexpressing cell types HeLa, A2058, and Bowes. An example of a cell which does not overexpress a plasminogen activator receptor is the non-tumor cell line Vero. An example of a cells that overexpress a tissue type plasminogen activator are cell types human melanoma Bowes and human primary vascular endothelial cells.

It will be appreciated by the skilled artisan that while cells overexpressing MMPs or plasminogen activator system proteins, such as cancer cells, can be targeted by the mutant protective antigen protein and lethal factor polypeptide compositions of the invention, some non-diseased cells that normally do not express these proteases are various physiological conditions to express MMPs or plasminogen activator system proteins, and thus are targeted. Moreover, cells that otherwise express basal levels of these proteinases may also be targeted.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

As used herein, the term "mutation" encompasses all possible types of modification of any given residue in a polynucleotide or polypeptide chain, including deletion, insertion, substitution, and chemical modification of the residue. While deletions and substitutions are the more common types of mutations, insertion of one or more residues at the a pre-determined location within a polynucleotide or polypeptide sequence is also within the scope of "mutation" as used in this application. Chemical modification of one or more side groups of any residues within a polynucleotide or polypeptide sequence is also within the meaning of a "mutation" in this application.

The term "heterologous" used herein refers to a relationship of at least two elements that is not found in nature. For example, when a recombinant fusion polypeptide is described as a first peptide (e.g., the first 254 amino acids of the native lethal factor protein) linked to a second "heterologous" peptide, it means the first and second peptides are not found in nature connected together in this order or fashion. Similarly, two elements (e.g., two shorter nucleotide sequences) within a polynucleotide sequence are "heterologous" to each other when these two elements are not found in nature to be connected in the manner they are placed in relation with each other in the polynucleotide chain.

As used herein, "a compound comprising a protective antigen binding site" is a molecule that binds to the protective antigen protein in the oligomeric form following the proteolytic cleavage of the N-terminal fragment of the protective antigen protein, which may be resulted from the enzymatic action of furin or another proteinase for which a corresponding cleavage site has been engineered into the protective antigen protein. For example, the N-terminal segment (e.g., the first 250 amino acids) of the anthrax lethal factor protein and edema factor protein is described as containing "a protective antigen binding site."

III. Anthrax Toxin

The symptoms of many bacterial diseases are due largely to the actions of toxic proteins released by the bacteria. Diphtheria toxin (DT) and *Pseudomonas* exotoxin A (PE) are two such well-known toxins secreted by the pathogenic bacterium *Corynebacterium diphtheriae* and the opportunistic pathogen *Pseudomonas aeruginosa* (Liu and Leppla, *Mol. Cell,* 12:603-613 (2003)). After binding and entering mammalian cells, DT and PE catalyze the adenosine diphosphate (ADP)-ribosylation and inactivation of elongation factor 2 (EF2), leading to protein synthesis inhibition and cell death (Collier, *Toxicon,* 39:1793-1803 (2001); Liu et al., *Mol. Cell Biol.,* 24:9487-9497 (2004)). The powerful lethal action of these toxins has been exploited extensively in the past two decades to target cancer cells by fusing the toxins with antibodies or growth factors that can selectively recognize antigens or receptors on cancer cells. These efforts have resulted in the first FDA-approved "immunotoxin," $DAB_{389}IL2$ (denileukin diftitox or Ontak), a fusion of DT catalytic and translocation domains and IL2 (interleukin 2), for treatment of persistent or recurrent T-cell lymphoma (Olsen, E., et al., *J. Clin. Oncol.,* 19:376-388 (2001)). With the rapid progress in understanding the structures and functions of anthrax lethal toxin (LT), an important virulence factor secreted by *Bacillus anthracis*, LT has been identified as a bacterial toxin having a completely different mode of action that can be used for tumor targeting (Liu and Leppla, *Mol. Cell,* 12:603-613 (2003)).

Anthrax toxin is a three-part toxin secreted by *Bacillus anthracis* consisting of protective antigen (PA, 83 kDa), lethal factor (LF, 90 kDa) and edema factor (EF, 89 kDa), which are individually non-toxic (see Leppla, (1991) The anthrax toxin complex, p. 277-302. In J. E. Alouf and J. H. Freer (ed.), *Sourcebook of bacterial protein toxins*. Academic Press, London, UK; Leppla, Anthrax toxins, *Handb. Nat. Toxins* 8:543-572 (1995). To manifest cytotoxicity to mammalian cells, PA binds to the cell surface receptors tumor endothelium marker 8 (TEM8) and capillary morphogenesis gene 2 product (CMG2). PA is proteolytically activated by cell surface furin protease by cleavage at the sequence $RKKR_{167}$ (SEQ ID NO:15), leaving the carboxyl-terminal 63 kDa fragment (PA63) bound to the cell surface, resulting in the formation of the active PA63 heptamer and PA20, a 20 kDa N-terminal fragment, which is released into the medium. The PA63 heptamer then binds and translocates LF into the cytosol of the cell to exert its cytotoxic effects (Leppla, *The Comprehensive Sourcebook of Bacterial Protein Toxins,* 323-347 (2006)). An NCI60 anticancer drug screen (Shoemaker, 2006) identified LF cellular targets as the mitogen-activated protein kinase kinases (MEK) 1 and 2 (Duesbery et al., *Science,* 280:734-737 (1998)). Later, the LF targets were extended to include MEK1 through 7, with the exception of MEK5 (Vitale et al., *Biochem. Biophys. Res. Commun.,* 248:706-711 (1998); Vitale et al., *Biochem. J.* 352 Pt 3:739-745 (2000)). LF is a metalloproteinase that enzymatically cleaves and inactivates these MEKs and thus efficiently blocks three key mitogen-activated protein kinase (MAPK) pathways, including the ERK, p38, and Jun N-terminus kinase (JNK) pathways (Baldari et al., *Trends Immunol.* 27:434-440 (2006)).

The PA63 heptamer is also able to bind EF. The combination of PA+EF, named edema toxin, disables phagocytes and probably other cells, due to the intracellular adenylate cyclase activity of EF (see, Klimpel et al., *Mol. Microbiol.* 13:1094-1100 (1994); Leppla et al., Bacterial Protein Toxins, p. 111-112 (1988) Gustav Fischer, New York, N.Y.; Leppla *Proc. Natl. Acad. Sci. USA.,* 79:3162-3166 (1982)).

LF and EF have substantial sequence homology in amino acid (aa) 1-250, and a mutagenesis study showed this region constitutes the PA-binding domain (Leppla (1995) Anthrax toxins, *Handb. Nat. Toxins* 8:543-572; Quinn et al., *J. Biol. Chem.,* 166:20124-20130 (1991)). Systematic deletion of LF fusion proteins containing the catalytic domain of *Pseudomonas* exotoxin A established that LF aa 1-254 (LFn) are sufficient to achieve translocation of "passenger" polypeptides to the cytosol of cells in a PA-dependent process (see Arora et al., *J. Biol. Chem.* 267:15542-15548 (1992); Arora et al., *J. Biol. Chem.* 268:3334-3341 (1993)). Accordingly, the term "LFn", as used herein, refers to a fragment of LF that retains the ability to bind PA and comprising amino acids 1-254. A highly cytotoxic LFn fusion to the ADP-ribosylation domain of *Pseudomonas* exotoxin A, named FP59, has been developed (Arora et al., *J. Biol. Chem.* 268: 3334-3341 (1993)). When combined with PA, FP59 kills any cell type which contains receptors for PA by the mechanism of inhibition of initial protein synthesis through ADP ribosylating inactivation of elongation factor 2 (EF-2), whereas native LF is highly specific for macrophages (Leppla, Anthrax toxins, *Handb. Nat. Toxins* 8:543-572 (1995)). For this reason, FP59 is an example of a potent therapeutic agent when specifically delivered to the target cells with a target-specific PA.

The crystal structure of PA at 2.1 Å was solved by X-ray diffraction (PDB accession 1ACC) (Petosa et al., *Nature* 385:833-838 (1997)). PA is a tall, flat molecule having four distinct domains that can be associated with functions previously defined by biochemical analysis. Domain 1 (aa 1-258) contains two tightly bound calcium ions, and a large flexible loop (aa 162-175) that includes the sequence $RKKR_{167}$ (SEQ ID NO:15), which is cleaved by furin during proteolytic activation. Domain 2 (aa 259-487) contains several very long β-strands and forms the core of the membrane-inserted channel. It is also has a large flexible loop (aa 303-319) implicated in membrane insertion. Domain 3 (aa 488-595) has no known function. Domain 4 (aa 596-735) is loosely associated with the other domains and is involved in receptor binding. Because cleavage at $RKKR_{167}$ (SEQ ID NO:15) is absolutely required for the subsequent steps in toxin action, it was of great interest to engineer it to the cleavage sequences of some disease-associated proteases, such as matrix metalloproteinases (MMPs) and plasminogen activators or receptors (e.g., t-PA, u-PA, and uPAR; see, e.g., Romer et al., *APMIS* 107:120-127 (1999)), which are typically overexpressed in tumors.

The unique requirement for PA proteolytic activation on the target cell surface provides a way to re-engineer this protein to make its cleavage dependent on proteases that are enriched in tumor tissues. To this end, PA mutants were previously generated requiring activation by matrix metalloproteinascs (MMPs) or by plasminogen activator (Liu et al., *Cancer Res.*, 60:6061-6067 (2000); Liu et al., *J Biol Chem* 276(21):17976-17984 (2001); and WO 01/21656) MMPs are overproduced by tumor tissues and implicated in cancer cell growth, angiogenesis, and metastasis (Egeblad and Werb, *Nat. Rev. Cancer,* 2:161-174 (2002)). Unlike furin, which is ubiquitously expressed, MMPs and plasminogen activators/plasminogen activator receptors are restricted to only a small number of normal cells. Overexpression of both is typically seen only in cancerous cells.

IV. MMPs and Plasminogen Activators

MMPs and plasminogen activators are families of enzymes that play a leading role in both the normal turnover and pathological destruction of the extracellular matrix, including tissue remodeling (Birkedal-Hansen *Curr. Opin. Cell Biol.,* 7:728-735 (1995); Alexander et al., *Development,* 122:1723-1736 (1996)), angiogenesis (Schnaper et al., *J. Cell Physiol.,* 156:235-246 (1993)), tumor invasion and metastasis formation. The members of the MMP family are multidomain, zinc-containing, neutral endopeptidases and include the collagenases, stromelysins, gelatinases, and membrane-type metalloproteinases (Birkedal-Hansen, *Curr. Opin. Cell Biol,* 7:728-735 (1995)). It has been well documented in recent years that MMPs and proteins of the plasminogen activation system, e.g., plasminogen activator receptors and plasminogen activators, are overexpressed in a variety of tumor tissues and tumor cell lines and are highly correlated to the tumor invasion and metastasis (Crawford et al., *Invasion Metastasis,* 14:234-245 (1995); Garbisa et al., *Cancer Res.,* 47:1523-1528 (1987); Himelstein et al., *Invest. Methods,* 14:246-258 (1995); Juarez et al., *Int. J. Cancer,* 55:10-18 (1993); Kohn et al., *Cancer Res.,* 55:1856-1862 (1995); Levy et al., *Cancer Res.,* 51:439-444 (1991); Mignatti et al., *Physiol. Rev.,* 73:161-195 (1993); Montgomery et al., *Cancer Res.,* 53:693-700 (1993); Stetler-Stevenson et al., *Annu. Rev. Cell Biol.,* 9:541-573 (1993); Stetler-Stevenson, *Invest. Methods,* 14:4664-4671 (1995); Davidson, et al., *Gynecol. Oncol.,* 73:372-382 (1999); Webber et al., *Carcinogenesis,* 20:1185-1192 (1999); Johansson et al., *Am. J. Pathol.,* 154:469-480 (1999); Ries et al., *Clin. Cancer Res.,* 5:1115-1124 (1999); Zeng et al., *Carcinogenesis,* 20:749-755 (1999); Gokaslan et al., *Clin. Exp. Metastasis,* 16:721-728 (1998); Forsyth et al., *Br. J. Cancer,* 79:1828-1 835 (1999); Ozdemir et al., *J. Urol.,* 161:1359-1 363 (1999); Nomura et al., *Cancer Res.,* 55:3263-3266 (1995); Okada et al., *Proc. Natl. Acad. Sci. USA,* 92:2730-2734 (1995); Sato et al., *Nature,* 370:61-65 (1994); Chen et al., *Ann. NY Acad. Sci.,* 878:361-371 (1999); Sato et al., *Br. J. Cancer,* 80:1137-43 (1999); Polette et al., *Int. J. Biochem. Cell Biol.,* 30:1195-1202 (1998); Kitagawa et al., *J. Urol.,* 160:1540-1545; Nakada et al., *Am. J. Pathol.,* 154:417-428 (1999); Sato et al., *Thromb. Haemost,* 78:497-500 (1997)).

Among the MMPs, MMP-2 (gelatinase A), MMP-9 (gelatinase B) and membrane-type 1 MMP (MT1-MMP) are reported to be most related to invasion and metastasis in various human cancers (Crawford et al., *Invasion Metastasis,* 14:234-245 (1995); Garbisa et al., *Cancer Res.,* 47:1523-1528 (1987); Himelstein et al., *Invest. Methods,* 14:246-258 (1 995); Juarez et al., *Int. J. Cancer,* 55:10-1 8 (1 993); Kohn et al., *Cancer Res.,* 55:1856-1 862 (1995); Levy et al., *Cancer Res.,* 51:439-444 (1991); Mignatti et al., *Physiol. Rev.,* 73:161-195 (1993); Montgomery et al., *Cancer Res.,* 53:693-700 (1993); Stetler-Stevenson et al., *Annu. Rev. Cell Biol.,* 9541-9573 (1993); Stetler-Stevenson *Invest. Methods,* 14:4664-4671 (1995); Davidson et al., *Gynecol. Oncol.,* 73:372-382 (1999); Webber et al., *Carcinogenesis,* 20:1185-1192 (1999); Johansson et al., *Am. J. Pathol.,* 154:469-480 (1999); Ries et al., *Clin. Cancer Res.,* 5:1115-1124 (1999); Zeng et al., *Carcinogenesis,* 20:749-755 (1999); Gokaslan et al., *Clin. Exp. Metastasis,* 16:721-728 (1998); Forsyth et al., *Br. J. Cancer,* 79:1828-1 835 (1999); Ozdemir et al., *J. Urol.,* 161:1359-1363 (1999); Nomura et al., *Cancer. Res.,* 55:3263-3266 (1995); Okada et al., *Proc. Natl. Acad. Sci. USA,* 92:2730-2734 (1995); Sato et al., *Nature,* 370:61-65 (1994); Chen et al., *Ann. NY Acad. Sci.,* 878:361-371 (1999); Sato et al., *Br J Cancer,* 80:1137-43 (1999); Polette et al., *Int. J. Biochem. Cell Biol.,* 30:1195-1202 (1998); Kitagawa et al., *J. Urol.,* 160:1540-1545; Nakada et al., *Am. J. Pathol.,* 154:417-428 (1999); Sato et al., *Thromb. Haemost,* 78:497-500 (1997)). The important role of MMPs during tumor invasion and metastasis is to break down tissue extracellular matrix and dissolution of epithelial and endothelial basement membranes, enabling tumor cells to invade through stroma and blood vessel walls at primary and secondary sites. MMPs also participate in tumor neoangiogenesis and are selectively upregulated in proliferating endothelial cells in tumor tissues (Schnaper et al., *J. Cell Physiol.,* 156:235-246 (1993); Chambers et al., *J. Natl. Cancer Inst.,* 89:1260-1270 (1997)). Furthermore, these proteases can contribute to the sustained growth of established tumor foci by the ectodomain cleavage of membrane-bound pro-forms of growth factors, releasing peptides that are mitogens for tumor cells and/or tumor vascular endothelial cells (Arribas et al., *J. Biol. Chem.*, 271:11376-11382 (1996); Suzuki et al., *J. Biol. Chem.*, 272:31730-31737 (1997)).

However, catalytic manifestations of MMP and plasminogen activators are highly regulated. For example, the MMPs are expressed as inactive zymogen forms and require activation before they can exert their proteolytic activities. The activation of MMP zymogens involves sequential proteolysis of N-terminal propeptide blocking the active site cleft, mediated by proteolytic mechanisms, often leading to an autoproteolytic event (Springman, E. B., et al., *Proc. Natl. Acad. Sci. USA*, 873364-368 (1990); Murphy, G., et al., *APMIS*, 107:38-44 (1999)). Second, a family of proteins, the tissue inhibitors of metalloproteinases (TIMPs), are correspondingly widespread in tissue distribution and function as highly effective MMP inhibitors (Ki ~$10^{-10}$ M) (Birkedal-Hansen, H., et al., *Crit. Rev. Oral Biol. Med.*, 4:197-250 (1993)). Though the activities of MMPs are tightly controlled, invading tumor cells that utilize the MMPs degradative capacity somehow circumvent these negative regulatory controls, but the mechanisms are not well understood.

The contributions of MMPs in tumor development and metastatic process lead to the development of novel therapies using synthetic inhibitors of MMPs (Brown, P. D., *Adv. Enzyme Regul.*, 35:293-301 (1995); Wojtowicz-Praga, S., et al., *J. Clin. Oncol.*, 16:2150-2156 (1998); Drummond, A. H., et al., *Ann. NY Acad. Sci.*, 30:228-235 (1999)). Among a multitude of synthetic inhibitors generated, Marimastat is already clinically employed in cancer treatment (Drummond, A. H., et al., *Ann. NY Acad. Sci.*, 30:228-235 (1999)).

As an alternate to the use of MMP inhibitors, a novel strategy was devised using modified PAs which could only be activated by MMPs or plasminogen activators to specially kill MMP- or and plasminogen activator-expressing tumor cells. PA mutants are constructed in which the furin recognition site is replaced by sequences susceptible to cleavage by MMPs or and plasminogen activators. When combined with LF or an LF fusion protein comprising the PA binding site, these PA mutants are specifically cleaved by cancer cells, exposing the LF binding site and translocating the LF or LF fusion protein into the cell, thereby specifically delivering compounds, e.g., a therapeutic or diagnostic agent, to the cell (see WO 01/21656).

Mutant PA molecules in which the furin cleavage site is replaced by an MMP or plasminogen activator cleavage site can be used to deliver compounds such as toxins to the target cell, thereby killing the cell or otherwise modifying cellular activities of the cell. The compounds have the ability to bind PA through their interaction with LF and are translocated by PA into the cell. The PA and LF-comprising compounds are administered to cells or subjects, preferably mammals, more preferably humans, using techniques known to those of skill in the art. Optionally, the PA and LF-comprising compounds are administered with a pharmaceutically acceptable carrier.

The compounds typically are either native LF or an LF fusion protein, i.e., those that have a PA binding site (approximately the first 250 amino acids of LF, Arora et al., *J. Biol. Chem.* 268:3334-3341 (1993)) fused to another polypeptide or compound so that the protein or fusion protein binds to PA and is translocated into the cell, causing cell death (e.g., recombinant toxin FP59, anthrax toxin lethal factor residue 1-254 fusion to the ADP-ribosylation domain of *Pseudomonas* exotoxin A). The fusion is typically chemical or recombinant. The compounds fused to LF include various therapeutic or diagnostic agents, e.g., native LF, a cytotoxin, a bacterial toxin, shiga toxin, A chain of diphtheria toxin, *Pseudomonas* exotoxin A, a protease, a growth factor, an enzyme, a detectable moiety, a chemical compound, a nucleic acid, or a fusion polypeptide, etc.

The mutant PA molecules of the invention can be further targeted to a specific cell by making mutant PA fusion proteins. In these mutant fusion proteins, the PA receptor binding domain is replaced by a protein such as a growth factor or other cell receptor ligand specifically expressed on the cells of interest. In addition, the PA receptor binding domain may be replaced by an antibody that binds to an antigen specifically expressed on the cells of interest.

These proteins provide a way to specifically kill target cells without serious damage to normal or non-target cells. This method can also be applied to non-cancer inflammatory cells that contain high amounts of cell-surface associated MMPs or plasminogen activators. These PA mutants are thus useful as therapeutic agents to specifically kill tumor cells.

The research group led by the present inventors has previously constructed two PA mutants, PA-L1 and PA-L2, in which the furin recognition site is replaced by sequences susceptible to cleavage by MMPs, especially by MMP-2 and MMP-9. When combined with FP59, these two PA mutant proteins specifically killed MMP-expressing tumor cells, such as human fibrosarcoma HT1080 and human melanoma A2058, but did not kill MMP non-expressing cells.

With respect to the plasminogen activation system, two plasminogen activators are known, the urokinase-type plasminogen activator (uPA) and the tissue-type plasminogen activator (tPA) (Dano et al., *APMIS*, 107:120-127 (1999)). uPA is a 52 kDa serine protease which is secreted as an inactive single chain proenzyme (pro-uPA) (Nielsen et al., *Biochemisty*, 21:6410-6415 (1982); Petersen et al., *J. Biol. Chem.*, 263:11189-11195 (1988)). The binding domain of pro-uPA is the epidermal growth factor-like amino-terminal fragment (ATF; aa 1-135, 15 kDa) that binds with high affinity (Kd=0.5 mM) to urokinase-type plasminogen activator receptor (uPAR) (Cubellis et al., *Proc. Natl. Acad. Sci. U.S.A.*, 86:4828-4832 (1989)), a GPI-linked receptor. uPAR is a 60 kDa three domain glycoprotein whose N-terminal domain 1 contains the high affinity binding site for ATF of pro-uPA (Ploug et al., *J. Biol. Chem.*, 266:1926-1933 (1991); Behrendt et al., *J. Biol. Chem.*, 266:7842-7847 (1991)). uPAR is overexpressed on a variety of tumors, including monocytic and myelogenous leukemias (Lanza et al., *Br. J. Haematol.*, 103:110-123 (1998); Plesner et al., *Am. J. Clin. Pathol.*, 102:835-841 (1994)), and cancers of the breast (Carriero et al., *Clin. Cancer Res.*, 3:1299-1308 (1997)), bladder (Hudson et al., *J. Natl. Cancer Inst.*, 89:709-717 (1997)), thyroid (Ragno et al., *Cancer Res.*, 58:1315-1319 (1998)), liver (De Petro et al., *Cancer Res.*, 58:2234-2239 (1998)), pleura (Shetty et al., *Arch. Biochem. Biophys.*, 356:265-279 (1998)), lung (Morita et al., *Int. J. Cancer*, 78:286-292 (1998)), pancreas (Taniguchi et al., *Cancer Res.*, 58:4461-4467 (1998)), and ovaries (Sier et al., *Cancer Res.*, 58:1843-1849 (1998)). Pro-uPA binds to uPAR by ATF, while the binding process does not block the catalytic, carboxyl-terminal domain. By association with uPAR, pro-uPA gets near to and subsequently activated by trace amounts of plasmin bound to the plasma membrane by cleavage of the single chain pro-uPA within an intra-molecular loop held closed by a disulfide bridge. Thus the active uPA consists of two chains (A+B) held together by this disulfide bond (Ellis et al., *J. Biol. Chem.*, 264:2185-2188 (1989)). Plasminogen is present at high concentration (1.5-2.0 µM) in plasma and interstitial fluids (Dano et al., *Adv. Cancer Res.*, 44:139-266 (1985)). Low affinity, high capacity binding of plasminogen to cell-surface proteins through the lysine binding sites of plasminogen kringles enhances considerably the rate of plasminogen activation by uPA (Ellis et al., *J. Biol. Chem.*, 264:2185-2188 (1989); Stephens et al., *J. Cell Biol.*, 108:1987-1995 (1989)). Active uPA has high specificity for the Arg560-Val561 bond in plasminogen, and cleavage between these residues gives rise to more plasmin that is referred to as "reciprocal zymogen activation" (Petersen *Eur. J. Biochem.*, 245:316-323 (1997)). The result of this system is efficient generation of active uPA and plasmin on cell surface. In this context, uPAR serves as a template for binding and localization of pro-uPA near to its substrate plasminogen on plasma membrane.

Unlike uPA, plasmin is a relatively non-specific protease, cleaving fibrin, as well as, many glycoproteins and proteoglycans of the extracellular matrix (Liotta et al., *Cancer Res.*, 41:4629-4636 (1981)). Therefore, cell surface bound plasmin mediates the non-specific matrix proteolysis which facilitates invasion and metastasis of tumor cells through restraining tissue structures. In addition, plasmin can activate some of the matrix metalloproteases which also degrade tissue matrix (Werb et al., *N. Engl. J. Med.*, 296:1017-1023 (1977); DeClerck et al., *Enzyme Protein*, 49:72-84 (1996)). Plasmin can also activate growth factors, such as TGF-β, which may further modulate stromal interactions in the expression of enzymes and tumor neo-angiogenesis (Lyons et al., *J. Cell Biol.*, 106:1659-1665 (1988)). Plasminogen activation by uPA is regulated by two physiological inhibitors, plasminogen activator inhibitor-1 and 2 (PAI-1 and PAI-2) (Cubellis et al., *Proc. Natl. Acad. Sci. U.S.A.*, 86:4828-4832 (1989); Ellis et al., *J. Biol. Chem.*, 265:9904-9908 (1990); Baker et al., *Cancer Res.*, 50:4676-4684 (1990)), by formation 1:1 complex with uPA. Plasmin generated in the cell surface plasminogen activation system is relatively protected from its principle physiological inhibitor α2-antiplasmin (Ellis et al., *J. Biol. Chem.*, 266:12752-12758 (1991)).

Cancer invasion is essentially a tissue remodeling process in which normal tissue is substituted with cancer tissue. Accumulated data from preclinical and clinical studies strongly suggested that the plasminogen activation system plays a central role in the processes leading to tumor invasion and metastasis (Andreasen et al., *Int. J. Cancer*, 72:1-22 (1 997); Chapman *Curr. Opin. Cell Biol.*, 9:714-724 (1997); Schmitt et al., *Thromb. Haemost.*, 78:285-296 (1997)). High levels of uPA, uPAR, and PAI-1 are associated with poor disease outcome (Schmitt et al., *Thromb. Haemost.*, 78:285-296 (1997)). In situ hybridization studies of tumor tissues has shown that usually cancer cells show highly expressed uPAR, while tumor stromal cells expressed pro-uPA, which subsequently binds to uPAR on the surface of cancer cells where it is activated and thereby generating plasmin (Pyke et al., *Am. J. Pathol.*, 138:1059-1067 (1991)). For the activation of pro-uPA is highly restricted to the tumor cell surface, it may be an ideal target for cancer treatment.

uPA and tPA possess an extremely high degree of structural similarity (Lamba et al., *J. Mol. Biol.*, 258:117-135 (1996); Spraggon et al., *Structure*, 3:681-691 (1995)), share the same primary physiological substrate (plasminogen) and inhibitors (PAI-1 and PAI-2) (Collen et al., *Blood*, 78:3114-3124 (1991)), and exhibit restricted substrate specificity. By using substrate phage display and substrate subtraction phage display approaches, recent investigations had identified substrates that discriminate between uPA and tPA, showing the consensus substrate sequences with high selectivity by uPA or tPA (Ke et al., *J. Biol. Chem.*, 272:20456-20462 (1997); Ke et al., *J. Biol. Chem.*, 272:16603-16609 (1997)). To exploit the unique characteristics of the uPA plasminogen system and anthrax toxin in the design of tumor cell selective cytotoxins, in the work described here, mutated anthrax PA proteins were constructed in which the furin site is replaced by sequences susceptible to specific cleavage by uPA. These uPAR/uPA-targeted PA proteins were activated selectively on the surface of uPAR-expressing tumor cells in the presence of pro-uPA, and caused internalization of a recombinant cytotoxin FP59 to selectively kill the tumor cells. Also, a mutated PA protein was generated which selectively killed tissue-type plasminogen activator expressing cells.

V. Methods of Producing PA Mutants and LF Polypeptides

A. Construction of Nucleic Acids Encoding PA Mutants and LF Polypeptides

PA includes a cellular receptor binding domain, a translocation domain, and an LF binding domain. The PA polypeptides of the invention have at least a translocation domain and an LF binding domain. In the present invention, mature PA (83 kDa) is one preferred embodiment for generating further mutants. In addition to full length recombinant PA, aminoterminal deletions up to the 63 kDa cleavage site or additions to the full length PA are useful. A recombinant form of processed PA is also biologically active and could be used in the present invention. PA fusion proteins in which the receptor binding domain has been deleted can also be constructed to target PA to specific cell types. Although the foregoing and the prior art describe specific deletion and structure-function analysis of PA, any biologically active form of PA can be used in the present invention.

Amino-terminal residues 1-254 of LF are sufficient for PA binding activity. Amino acid residues 199-253 may not all be required for PA binding activity. One embodiment of LF is amino acids 1-254 of native LF. Any embodiment that contains at least about amino acids 1-254 of native LF can be used in the present invention, for example, native LF. Nontoxic embodiments of LF are preferred.

PA and LF fusion proteins can be produced using recombinant nucleic acids that encode a single-chain fusion protein. The fusion protein can be expressed as a single chain using in vivo or in vitro biological systems. Using current methods of chemical synthesis, compounds can be also be chemically bound to PA or LF. The fusion protein can be tested empirically for receptor binding, PA or LF binding, and internalization using methods as set forth, for example in WO 01/21656.

In addition, functional groups capable of forming covalent bonds with the amino- and carboxyl-terminal amino acids or side groups of amino acids are well known to those of skill in the art. For example, functional groups capable of binding the terminal amino group include anhydrides, carbodiimides, acid chlorides, and activated esters. Similarly, functional groups capable of forming covalent linkages with the terminal carboxyl include amines and alcohols. Such functional groups can be used to bind compound to LF at either the amino- or carboxyl-terminus. Compound can also be bound to LF through interactions of amino acid residue side groups, such as the SH group of cysteine (see, e.g., Thorpe et al., *Monoclonal Antibody-Toxin Conjugates: Aiming the Magic Bullet*, in *Monoclonal Antibodies in Clinical Medicine*, pp. 168-190 (1982); Waldmann, *Science*, 252:1657 (1991); U.S. Pat. Nos. 4,545,985 and 4,894,443). The procedure for attaching an agent to an antibody or other polypeptide targeting molecule will vary according to the chemical structure of the agent. As an example, a cysteine residue can be added at the end of LF. Since there are no other cysteines in LF, this single cysteine provides a convenient attachment point through which to chemically conjugate other proteins through disulfide bonds. Although certain of the methods of the invention have been described as using LF fusion proteins, it will be understood that other LF compositions having chemically attached compounds can be used in the methods of the invention.

Modified protective antigen proteins can be produced from nucleic acid constructs encoding mutants, in which the naturally occurring furin cleavage site has been replaced by an MMP or a plasminogen activator cleavage site and which contains at least one mutation at another location of the protective antigen protein, such as at residues 512, 245, and/or 252). In addition, LF proteins, and LF and PA fusion proteins can also be expressed from nucleic acid constructs according to standard methodology. Those of skill in the art will recognize a wide variety of ways to introduce mutations into a nucleic acid encoding protective antigen or to construct a mutant protective antigen-encoding nucleic acid. Such methods are well known in the art (see Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)). In some embodiments, nucleic acids of the invention are generated using polymerase chain reaction (PCR). For example, using overlap PCR protective antigen encoding nucleic acids can be generated by substituting the nucleic acid subsequence that encodes the furin site with a nucleic acid subsequence that encodes a matrix metalloproteinase (MMP) site (e.g., GPLGMLSQ (SEQ ID NO:9) and GPLGLWAQ (SEQ ID NO:10)). Similarly, an overlap PCR method can be used to construct the protective antigen proteins in which the furin site is replaced by a plasminogen activator cleavage site (e.g., the uPA and tPA physiological substrate sequence PCPGRVVGG (SEQ ID NO:11), the uPA favorite sequence PGSGRSA (SEQ ID NO:12), the uPA favorite sequence PGSGKSA (SEQ ID NO:13), or the tPA favorite sequence PQRGRSA (SEQ ID NO:14)) (see, e.g., WO 01/21656).

B. Expression of Mutant PA and LF Polypeptides

To obtain high level expression of a nucleic acid (e.g., cDNA, genomic DNA, PCR product, etc. or combinations thereof) encoding a native (e.g., PA) or mutant protective antigen protein (e.g., PA-L1, PA-L2, PA-U1, PA-U2, PA-U3, PA-U4, etc.), LF, or a PA or LF fusion protein, one typically subclones the protective antigen encoding nucleic acid into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al., supra and Ausubel et al., supra. Bacterial expression systems for expressing the protective antigen encoding nucleic acid are available in, e.g., *E. coli, Bacillus* sp., and *Salmonella* (Palva et al., *Gene* 22:229-235 (1983)). Kits for such expression systems are commercially available. Eukaryotic expression systems for mammalian cells, yeast, and insect cells are well known in the art and are also commercially available.

In some embodiments, protective antigen mutants are expressed in non-virulent strains of *Bacillus* using *Bacillus* expression plasmids containing nucleic acid sequences encoding the particular protective antigen protein (see, e.g., Singh et al., *J. Biol. Chem.*, 264:19103-19107 (1989)). The protective antigen mutants can be isolated from the *Bacillus* culture using protein purification methods (see, e.g., Varughese et al., *Infect. Immun.*, 67:1860-1865 (1999)).

The promoter used to direct expression of a protective antigen encoding nucleic acid depends on the particular application. The promoter is preferably positioned about the same distance from the heterologous transcription start site as it is from the transcription start site in its natural setting. As is known in the art, however, some variation in this distance can be accommodated without loss of promoter function. The promoter typically can also include elements that are responsive to transactivation, e.g., Gal4 responsive elements, lac repressor responsive elements, and the like. The promoter can be constitutive or inducible, heterologous or homologous.

In addition to the promoter, the expression vector typically contains a transcription unit or expression cassette that contains all the additional elements required for the expression of the nucleic acid in host cells. A typical expression cassette thus contains a promoter operably linked, e.g., to the nucleic acid sequence encoding the protective antigen containing protein, and signals required for efficient expression and termination and processing of the transcript, ribosome binding sites, and translation termination. The nucleic acid sequence may typically be linked to a cleavable signal peptide sequence to promote secretion of the encoded protein by the transformed cell. Such signal peptides would include, among others, the signal peptides from bacterial proteins, or mammalian proteins such as tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination and processing, if desired. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown to be effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as using a baculovirus vector in insect cells, with a protective antigen encoding nucleic acid under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of heterologous sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of protein, which are then purified using standard techniques (see, e.g., Colley et al., *J. Biol. Chem.* 264:17619-17622 (1989); *Guide to Protein Purification, in Methods in Enzymology*, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss and Curtiss, *Methods in Enzymology* 101:347-362 (Wu et al., eds. 1983).

Any of the well-known procedures for introducing foreign nucleotide sequences into host cells may be used. These include the use of calcium phosphate transfection, polybrene, protoplast fusion, electroporation, liposomes, microinjection, plasma vectors, viral vectors and any of the other well-known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.

After the expression vector is introduced into the cells, the transfected cells are cultured under conditions favoring expression of the protective antigen containing protein, which is recovered from the culture using standard techniques identified below.

VI. Purification of Polypeptides of the Invention

Recombinant proteins of the invention can be purified from any suitable expression system, e.g., by expressing the proteins in *B. anthracis* and then purifying the recombinant protein via conventional purification techniques (e.g., ammonium sulfate precipitation, ion exchange chromatography, gel filtration, etc.) and/or affinity purification, e.g., by using antibodies that recognize a specific epitope on the protein or on part of the fusion protein, or by using glutathione affinity gel, which binds to GST (see, e.g., Scopes, *Protein Purification: Principles and Practice* (1982); U.S. Pat. No. 4,673,641; Ausubel et al., supra; and Sambrook et al., supra). In some embodiments, the recombinant protein is a fusion protein with GST or Gal4 at the N-terminus. Those of skill in the art will recognize a wide variety of peptides and proteins that can be fused to the protective antigen containing protein to facilitate purification (e.g., maltose binding protein, a polyhistidine peptide, etc.).

A. Purification of Recombinant Proteins

Recombinant proteins can be expressed by transformed bacteria in large amounts, typically after promoter induction; but expression can be constitutive. Promoter induction with IPTG is one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of inclusion bodies. For example, purification of inclusion bodies typically involves the extraction, separation and/or purification of inclusion bodies by disruption of bacterial cells, e.g., by incubation in a buffer of 50 mM Tris/HCl pH 7.5, 50 mM NaCl, 5 mM $MgCl_2$, 1 mM DTT, 0.1 mM ATP, and 1 mM PMSF. The cell suspension can be lysed using 2-3 passages through a French press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. The protein of choice is separated from other bacterial proteins by standard separation techniques, e.g., ion exchange chromatography, ammonium sulfate fractionation, etc.

B. Standard Protein Separation Techniques for Purifying Proteins of the Invention (1) Solubility Fractionation Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. Alternatively, the protein of interest in the supernatant can be further purified using standard protein purification techniques. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

(2) Size Differential Filtration

The molecular weight of a recombinant protein, e.g., a mutant protective antigen protein, can be used to isolated the protein from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

(3) Column Chromatography

The protein of interest can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

In some embodiments, the recombinant proteins are purified from culture supernatants of *Bacillus*. Briefly, the proteins are purified by making a culture supernatant 5 mM in EDTA, 35% saturated in ammonium sulfate and 1% in phenyl-Sepharose Fast Flow (Pharmacia). The phenyl-Sepharose Fast Flow is then agitated and collected. The collected resin is washed with 35% saturated ammonium sulfate and the protective antigens were then eluted with 10 mM HEPES-1 mM EDTA (pH 7.5). The proteins can then be further purified using a MonoQ column (Pharmacia Biotech). The proteins can be eluted using a NaCl gradient in 10 mM CHES (2-[N-cyclohexylamino]ethanesulfonic acid)-0.06% (vol/vol) ethanolamine (pH 9.1). The pooled MonoQ fractions can then be dialyzed against the buffer of choice for subsequent analysis or applications.

VII. Assays for Measuring Effective Delivery

The administration of a functional combination comprising two PA mutants and a compound to be delivered to target cells, such as a LF polypeptide, according to the present invention can exhibit the intended effects, for example, inhibition of cellular proliferation of the target cell types that overexpress two different proteinases (e.g., a plasminogen activator and a matrix metalloproteinase). One of skill in the art can readily identify functional combination of two PA mutant proteins and an effector compound be studying the effects on the target cells using methods that are well known in the art as well as those described herein. When LF is used, target cell proliferation rate is assessed by using a variety of in vitro and in vivo assays, e.g., MTT assay, to determine the effectiveness of the two-protective antigen mutant delivery system. Other assays may be used to assess effectiveness by observing changes in target cells' ability to grow on soft agar, changes in contact inhibition and density limitation of growth, changes in growth factor or serum dependence, changes in the level of tumor specific markers, changes in invasiveness into Matrigel, changes in cell cycle pattern, changes in tumor growth in vivo, such as in normal and transgenic mice, etc.

One or more of the following assays designed to detect changes in cell proliferation can be used to identify mutant protective antigen proteins of the invention that are capable of successfully delivery of an effector compound to a target cell population. Functional protective antigen mutants and their combinations identified by the following assays can then be used to regular cellular and biological activities in the target cells and potentially to treat pertinent disease and conditions, e.g., to inhibit abnormal cellular proliferation and transformation. Thus, these assays can be used to identify protective antigen protein variants that are useful in conjunction with an effector compound (such as a lethal factor polypeptide) to inhibit cell proliferation of tumors, cancers, and other pathogenic cell types. Description of various assays can be found in, e.g., WO2008/076939.

(1) Soft Agar Growth or Colony Formation in Suspension

Soft agar growth or colony formation in suspension assays can be used to identify protective antigen variants, which when used in conjunction with a LF construct, inhibit abnormal cellular proliferation and transformation. Typically, transformed host cells (e.g., cells that grow on soft agar) are used in this assay. Techniques for soft agar growth or colony formation in suspension assays are described in Freshney, *Culture of Animal Cells a Manual of Basic Technique,* 3rd ed., Wiley-Liss, New York (1994). See also, the methods section of Garkavtsev et al. (1996), supra.

Normal cells require a solid substrate to attach and grow. When the cells are transformed, they lose this phenotype and grow detached from the substrate. For example, transformed cells can grow in stirred suspension culture or suspended in semi-solid media, such as semi-solid or soft agar. The transformed cells, when transfected with tumor suppressor genes, regenerate normal phenotype and require a solid substrate to attach and grow.

Administration of a functional combination of two protective antigen mutants and an active LF containing protein (e.g., a native LF protein or FP59) to transformed cells would reduce or eliminate the host cells' ability to grow in stirred suspension culture or suspended in semi-solid media, such as semi-solid or soft. This is because the transformed cells would regenerate anchorage dependence of normal cells, and therefore require a solid substrate to grow. Therefore, this assay can be used to identify protective antigen constructs that can function with a lethal factor protein to inhibit cell growth. Once identified, such protective antigen constructs can be used in a number of diagnostic or therapeutic methods, e.g., in cancer therapy to inhibit abnormal cellular proliferation and transformation.

(2) Contact Inhibition and Density Limitation of Growth

Contact inhibition and density limitation of growth assays can be used to identify functional combination of two different protective antigen mutants that are capable of delivering an active LF polypeptide to inhibit abnormal proliferation and transformation in host cells. Typically, transformed host cells (e.g., cells that are not contact inhibited) are used in this assay. Administration of a protective antigen construct and a lethal factor construct to these transformed host cells would result in cells which are contact inhibited and grow to a lower saturation density than the transformed cells. Therefore, this assay can be used to identify protective antigen constructs which are useful in compositions for inhibiting cell growth. Once identified, such protective antigen constructs can be used in disease therapy to inhibit abnormal cellular proliferation and transformation.

Alternatively, labeling index with [$^3$H]-thymidine at saturation density can be used to measure density limitation of growth. See Freshney (1994), supra. The transformed cells, when treated with a functional PA mutants/LF combination, regenerate a normal phenotype and become contact inhibited and would grow to a lower density. In this assay, labeling index with [$^3$H]-thymidine at saturation density is a preferred method of measuring density limitation of growth. Transformed host cells are treated with two protective antigen mutants and a lethal factor polypeptide (e.g., FP59) and are grown for 24 hours at saturation density in non-limiting medium conditions. The percentage of cells labeling with [$^3$H]-thymidine is determined autoradiographically. See, Freshney (1994), supra. The host cells treated with a functional protective antigen construct would give arise to a lower labeling index compared to control (e.g., transformed host cells treated with a non-functional protective antigen construct or non-functional lethal factor construct).

(3) Growth Factor or Serum Dependence

Growth factor or serum dependence can be used as an assay to identify functional combination of protective antigen mutants. Transformed cells have a lower serum dependence than their normal counterparts (see, e.g., Temin, *J. Natl. Cancer Insti.* 37:167-175 (1966); Eagle et al., *J. Exp. Med.* 131:836-879 (1970)); Freshney, supra. This is in part due to release of various growth factors by the transformed cells. When a tumor suppressor gene is transfected and expressed in these transformed cells, the cells would reacquire serum dependence and would release growth factors at a lower level. Therefore, this assay can be used to identify different protective antigen mutants which are able to act in conjunction with a lethal factor to inhibit cell growth. Growth factor or serum dependence of transformed host cells which are transfected with a protective antigen construct can be compared with that of control (e.g., transformed host cells which are treated with a non-functional protective antigen or non-functional lethal factor). Transformed host cells treated with a functional protective antigen would exhibit an increase in growth factor and serum dependence compared to control.

Additional assays designed to detect changes in angiogenesis and endothelia cell migration may also be used for identifying functional combination of protective antigen mutants. WO2008/076939 provides a detailed description of these assays, including assays that directly measure endothelial cell proliferation, assays that measure endothelial cell migration or tube formation, organ culture assays, as well as a number of in vivo assays, such as the chick chorioallantoic membrane (CAM) assay, an in vivo Matrigel plug assay, and a group of assays that use implants of sponges containing test cells or substances.

VIII. Pharmaceutical Compositions and Administration

The modified protective antigen proteins of this invention and a compound intended to be delivered to a target cell (e.g., a lethal factor polypeptide containing all or a portion of the native LF and capable of binding to an oligomer of protective antigen proteins after proteolytic cleavage of the protective antigen proteins) can be administered directly to the patient, e.g., for inhibition of cancer, tumor, or precancer cells in vivo, or for suppression or elimination of certain undesirable cell populations. Administration is by any of the routes normally used for introducing a compound into ultimate contact with the tissue to be treated. The compounds are administered in any suitable manner, preferably with pharmaceutically acceptable carriers. Suitable methods of administering such compounds are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington's Pharmaceutical Sciences*, 17th ed. 1985)). For example, if in vivo delivery of a biologically active protective antigen protein is desired, the methods described in Schwarze et al. (see, *Science* 285: 1569-1572 (1999)) can be used.

The compounds of this invention (i.e., the at least two different protective antigen mutants, the effector molecule to be delivered to the target cells), alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically, intranasally, or intrathecally. The formulations of compounds can be presented in unit-dose or multi-dose sealed containers, such as ampules and vials. Injection solutions and suspensions can be prepared from sterile powders, granules, and tablets of the kind previously described.

Furthermore, the compounds of this invention (i.e., the at least two different protective antigen mutants, the effector molecule to be delivered to the target cells), can be administered to a recipient, e.g., a human patient, either together (e.g., compounds present in the same composition or in separate compositions but given to the recipient simultaneously or nearly simultaneously, for instance, within the hour of administration of other compounds) or separately (e.g., administered in separate compositions and at different times, typically more than 2, 3, 4, 5, 6, 7, 8, 9, 10, 12, or more hours apart, or even via different routes). For example, the two protective antigen protein mutants may be administered up to 6 or 12 hours after the effector compound (such as the lethal factor protein or FP59) is administered. In some cases, it is possible to administer to a patient the effector compound (e.g., LF or FP59) by intravenous infusion. Up to 6 or 12 hours later the protective antigen mutants can then be administered to the patient either by intravenous infusion or alternative routes such as intratumoral injection.

The dose administered to a patient ("a therapeutically effective amount" or simply "an effective amount"), in the context of the present invention should be sufficient to effect a beneficial therapeutic response in the patient over time. The dose will be determined by the efficacy of the particular compound employed and the condition of the patient, as well as the body weight or surface area of the patient to be treated. The size of the dose also will be determined by the existence, nature, and extent of any adverse side-effects that accompany the administration of a particular compound or vector in a particular patient.

In determining the effective amount of the compound(s) to be administered in the treatment or prophylaxis of cancer, the physician evaluates circulating plasma levels of the respective compound(s), progression of the disease, and the production of anti-compound antibodies. In general, the dose equivalent of a compound can range from about 1 ng/kg to 10 mg/kg body weight for a typical patient. For example, an effective dose in human administration may include 2.5 to 75 µg/kg of a first protective antigen mutant, 2.5 to 75 µg/kg of a second protective antigen mutant, and 2.5 to 75 µg/kg of an effector compound (e.g., a lethal factor protein), administered six times over the course of two weeks. It is also possible to administer to human patients in a dosing range of 0.25 to 1 mg/kg in a similar schedule. Administration of compounds is well known to those of skill in the art (see, e.g., Bansinath et al., *Neurochem. Res.* 18:1063-1066 (1993); Iwasaki et al., *Jpn. J. Cancer Res.* 88:861-866 (1997); Tabrizi-Rad et al., *Br. J. Pharmacol.* 111:394-396 (1994)).

For administration, compounds of the present invention can be administered at a rate determined by the LD-50 of the particular compound, and its side-effects at various concentrations, as applied to the mass and overall health of the patient. Administration can be accomplished via single or divided doses.

EXAMPLES

The following examples are provided by way of illustration only and not by way of limitation. Those of skill in the art will readily recognize a variety of non-critical parameters that could be changed or modified to yield essentially the same or similar results.
Introduction

*Bacillus anthracis* is a Gram-positive, spore-forming bacterium that is the causative agent of anthrax. Anthrax toxicity is mediated through its poly-D-glutamic acid capsule (Fouet (2009) *Mol Aspects Med* 30(6):374-385) and its tripartite toxin. The toxin is composed of protective antigen (PA), lethal factor (LF), and edema factor (EF) (for review, see (Moayeri and Leppla (2009) *Mol Aspects Med* 30(6): 439-455; Young and Collier (2007) *Annu Rev Biochem* 76:243-265). PA binds to the cellular receptors CMG2 and TEM8, and the 83-kDa protein is cleaved by furin to a 63-kDa form ($PA_{63}$) which then oligomerizes. Formation of an oligomer generates LF/EF binding sites at the interface of two adjacent PA molecules. PA oligomerization also initiates receptor-based signaling that triggers endocytosis of the complex. Upon acidification of the endosome, the PA oligomer forms a pore in the endosomal membrane through which the LF and EF proteins transit. Once in the cytosol, these effector proteins exert their catalytic activities. EF is a calmodulin-dependent adenylyl cyclase (Leppla (1982) *Proc Natl Acad Sci USA* 79(10):3162-3166) that aids in dissemination of *B. anthracis* in the host (Dumetz et al. (2011) *Am J Pathol* 178(6):2523-2535). LF is a zinc metalloprotease that cleaves mitogen-activated protein kinase kinases (Duesbery et al. (1998) *Science* 280(5364):734-737; Vitale et al., (2000) *Biochem J* 352 Pt 3:739-745) and N1rp1 (Levinsohn et al. (2012) *PLoS Pathog* 8(3):e1002638), thereby perturbing signal transduction in host cells.

It has long been observed that PA forms a heptamer upon furin cleavage, and that oligomerization is required for toxicity (Milne et al., (1994) *J Biol Chem* 269(32):20607-20612). Recently, it has been shown by Krantz and colleagues that PA is also capable of forming functional octamers (Kintzer et al. (2009) *J Mol Biol* 392:614-629). Conditions under which octameric oligomerization predominates were exploited to crystallize the octamer (Kintzer et al. (2009) *J Mol Biol* 392:614-629). Comparison of the octamer and heptamer crystal structures revealed that there are two orientations of PA domain 4 (the receptor-binding domain) that alternate in the octamer to accommodate the new geometry. Constraining the location of PA domain 4 using different linkers connected to the remainder of the protein altered the proportion of octamers and heptamers that formed (Feld et al., (2011) *J Mol Biol* 415(1):159-174).

The present inventors set out to create PA variants that would selectively and exclusively form octamers, starting with the PA mutant D512K (Mogridge et al., (2002) *Proc Natl Acad Sci USA* 99(10):7045-7048), which is incapable of forming oligomers (FIG. 1A). A library of PA variants having the D512K substitution together with random mutations in several residues on the complementary face of $PA_{63}$ within the oligomers (FIG. 1B) was prepared and screened for a (re)gain of function. Screening of this library successfully identified mutations that complement D512K. The inventors next placed D512K and the new complementary mutations into two separate PA proteins, so that formation of oligomers through the use of the two unique interfaces (wild type and mutated) resulted in only even-numbered oligomers, among which octamer was expected to predominate (FIG. 1C). Furthermore, the octamer strategy was applied to create a tumor-targeting agent having high specificity.
Materials and Methods
Plasmids Plasmid pYS2-PA-D512K was created through site-directed mutagenesis of pYS2 (Singh et al. (1989) *J Biol Chem* 264(32):19103-19107) by GMBiosciences (Rockville, Md.). The pagA gene fragment containing the D512K point mutation between the PstI and BamHI sites was moved into pYS5 (Singh et al. supra) by digestion of both vectors with PstI and BamHI with additional cleavage of the pYS5 pagA gene with SwaI and cleavage of the pYS2-PA-D512K vector backbone with FspI (blunt cutting enzymes were used to prevent alternative ligation products) followed by ligation. Plasmids were electroporated into *E. coli* XL1-Blue (Agilent Technologies, Santa Clara, Calif.), sequenced, then electroporated successively into *E. coli* strain SCS110 (Agilent Technologies) and BH460, an acapsular, nontoxogenic, protease-deficient, protein overexpression *B. anthracis* strain (Pomerantsev et al. (2011) *Protein Expr Purif* 80(1):80-90).

Reversion of the D512K point mutation to wild type in PA variants recovered from the screen was performed with Quikchange Multi Site-Directed Mutagenesis kit (Agilent Technologies) using the manufacturer's protocol. The primer used for reversion was GGATAGCGGCGGT-TAATCCTAGT<u>GAT</u>CCATTAGAAACGACTAA (SEQ ID NO:1). Vectors used to express PA-L1-GN, PA-L1-NS, and PA-U2-D512K were constructed by placing D512K or the newly isolated mutations into existing PA variants PA-L1 and PA-U2 using Quikchange Multi Site-Directed Mutagenesis kit in a similar manner. PA-U2-D512K was constructed using GGATAGCGGCGGTTAATCCTAGT<u>AAG</u>CCATTAGAAACGACTAA (SEQ ID NO:2) with pYS5-PA-U2. PA-L1-GN and PA-L1-NS were constructed using pYS5-PA-L1 with GGTTACAGGACGGATTGAT GG<u>AA</u>ATGTATCACCAGAGGCA<u>AAC</u>CACCCCTTG (SEQ ID NO:3) and GGTTACAGGACGGATTGAT <u>AAC</u>AATGTATCACCAGAGGCA<u>AGC</u>CACCCCTTG (SEQ ID NO:4), respectively.
Proteins PA variants (Varughese et al. (1998) *Mol Med* 4(2):87-95), LF (Park and Leppla (2000) *Protein Expr Purif* 18(3):293-302), and FP59 (Varughese et al. supra) were expressed and purified as described previously. Expected molecular weights of all proteins were confirmed by electrospray ionization (ESI) mass spectrometry. FP59 is a fusion protein of the N-terminal 254 amino acids of LF, which is the PA binding domain, fused to the catalytic domain of *Pseudomonas* exotoxin A, which ADP-ribosylates eukaryotic elongation factor 2 to inhibit protein synthesis, leading to cell death. This fusion protein has been shown to be more toxic to most cells than LF in combination with PA. All toxin doses used in these studies were selected based on previous work.

Library Construction, Screening, and Tissue Culture Studies

The library containing RRM degenerate codons at PA amino acid positions K238, R242, K245, and 8252 was constructed using overlap extension PCR (Ho et al., (1989) *Gene* (Amst.) 77:51-59) Inner primers were CTTCTGATCCGTACAGTGATTTCGAARRMGTTACAGGA RRMATTGATRRMAATG TATCACCAGAGGCA RRMCACCCCCTTGTGGCAGC (forward, SEQ ID NO:5) and TTCGAAATCACTGTACGGATCAGAAG (reverse, SEQ ID NO:6), whereas outer primers used for both primary and secondary amplifications were GACGAGCGCTTCGGTCTTAACTG (forward, SEQ ID NO:7) and AGCAGCCAACTCAGCTTCCTTTCG (reverse, SEQ ID NO:8). The amplicon was cut with BstXI and BamHI and ligated into pYS5-PA-D512K. Purified plasmid was transformed successively into electrocompetent cell strains MC1061 (ATCC, Manassas, Va.), SCS110, and BH460. At each step, transformed cells were placed at 37° C. overnight on LB agar plates containing 100 µg/mL carbenicillin for *E. coli* strains, and 10 µg/mL kanamycin for BH460. After overnight growth, plates were scraped and plasmid was isolated. Transformation into MC1061 produced a library of $4 \times 10^5$ clones, a 97-fold coverage of the theoretical library size. Introduction into SCS110 gave $2.5 \times 10^4$ clones, or 6-fold coverage. Each single electroporation reaction into BH460 yielded 400 colonies, or approximately 0.1-fold coverage. BH460 colonies were picked and placed into individual wells on 96-well plates (Corning) and grown overnight at 37° C. in FA medium (Singh et al., supra). Plates were centrifuged to pellet the bacteria, and 2 µL was withdrawn from each well for screening.

RAW264.7 cells, a mouse macrophage cell line, were used to assess toxicity of PA variants. Cells were plated the night before a screening experiment at 50,000 cells per well, and grown overnight at 37° C. in a humidified atmosphere with 5% $CO_2$ in Dulbecco's modified Eagle's medium (DMEM) with Glutamax (Invitrogen, Carlsbad, Calif.) supplemented with 10% fetal bovine serum, 10 mM HEPES buffer pH 7.3, 1 mM sodium pyruvate, and 10 µg/mL gentamycin (complete DMEM medium). The following day, the supernatant was aspirated and 100 µL of complete DMEM medium supplemented with 1.8 nM FP59 was placed on the cells in addition to the 2 µL of BH460 supernatant per well. Plates were placed at 37° C. for 24 h, and then viability was assessed using a 1-h incubation at 37° C. with 100 µL of complete DMEM medium supplemented with 2.5 mg/mL 3-(4,5-dimethyl-2-thiazolyl)-2,5-diphenyl-2H-tetrazolium bromide (MTT). After aspiration of the supernatant, thiazolium salts were solubilized in 91% isopropanol, 0.038 M HCl, and 0.476% SDS, then read at 570 nm. Tissue culture studies were performed similarly, but with purified PA variants mixed with FP59 instead of bacterial supernatants and in the presence or absence of protease inhibitors. Nafamostat mesylate (Sigma, St. Louis, Mo.) was used at a concentration of 75 µM, while Ilomastat (US Biological, Swampscott, Mass.) was used at a final concentration of 25 µM.

Animal Studies

C57BL/6J or Balb/cJ mice (8-12 weeks old, female, 20-25 g) were purchased from Jackson Laboratories (Bar Harbor, Me.). For survival studies with LF as effector, Balb/cJ mice (n=10/group) were injected intravenously (IV, 200 µL) with single PA variants (50 µg)+LF (50 µg). When the two PA variants were being tested in combination, each variant was used at 25 µg (for a total of 50 µg of PA), and combined with LF (50 µg). For survival studies with FP59 as effector, C57BL/6J mice were injected intraperitoneally (i.p., 1 ml) with single PA variants (10 µg)+FP59 (10 µg). When two PA variants were being tested in combination, each variant was used at 5 µg (for a total of 10 µg of PA) and combined with FP59 (10 µg). In experiments designed to test toxicity of the PA variants in the absence of effector proteins, the same dose of PA described above were injected into mice without LF or FP59. All animals were observed every 8-12 h for signs of malaise over a 7-day period.

For tumor studies, female, age-matched nude mice (NCI-Frederick Mouse Repository) were injected intradermally with $1 \times 10^6$ or $5 \times 10^6$ A549 cells and tumor growth was monitored. When tumors reached approximately 50 mg, mice (n=10) were injected IP with 6 doses of either PBS or PA variants and LF in a 2:1 mass ratio of PA:LF on days 0, 2, 4, 7, 9, and 11. Tumor size and body weight were measured on these days. When testing a combination of two PA variants, a 1:1:1 mass ratio of PA variant 1:PA variant 2:LF was administered. One animal died under anesthesia and was removed from the study. Maximum tolerated dose studies were conducted using an identical administration schedule with C57BL/6J and nude mice, and blood chemistry analysis was conducted by the Clinical Center, NIH. All mouse experiments were performed under protocols approved by the Animal Care and Use Committee of the National Institute of Allergy and Infectious Diseases, National Institutes of Health.

Electron Microscopy and Image Analysis

Aliquots of PA oligomer preparations (5 µL) were briefly applied to freshly glow-discharged, carbon-coated, 200-mesh copper grids, and excess removed by wicking with filter paper. Grids were then stained for 2 min with Nano-van (Nanoprobes, Inc., Yaphank, N.Y.), and prepared and examined under cryo conditions at 300 kV with a FEG Titan Krios transmission electron microscope (FEI, Hillsboro, Oreg.). Images were recorded at a nominal magnification of 120 kX and an electron dose of approximately 300 $e^-/Å^2$ to prevent radiation damage. Particles having axial orientation with a defocus range of approximately 0.5-2.5 µm were boxed with EMAN2, and then processed using the standard multi-reference free alignment to produce class averages with full contrast transfer function (CTF) correction without imposed symmetry.

Analytical Ultracentrifugation

Samples of protective antigen and its complex with lethal factor were prepared in 0.3 M NaCl, 0.01 M Bis-Tris Propane (pH 9.0) and 0.5 mM EDTA. Sedimentation velocity experiments were conducted at 20.0° C. on a Beckman Coulter ProteomeLab XL-I analytical ultracentrifuge. Samples of 400 µL were loaded in 2-channel centerpiece cells and analyzed at a rotor speed of 25,000 rpm with data collected using both the absorbance and Rayleigh interference optical detection systems. In the latter case, data were collected as single scans at 250 nm using a radial spacing of 0.003 cm. Absorbance and interference data were individually analyzed in SEDFIT 12.7 (Schuck (2000) *Biophys J* 78(3):1606-1619) in terms of a continuous c(s) distribution of Lamm equation solutions using an uncorrected s range of 0.0-30.0 S with a resolution of 300 and a confidence level of 0.68. In all cases, excellent fits were obtained with absorbance and interference r.m.s.d. values of 0.0026-0.0090 $A_{280}$ and 0.0054-0.015 fringes, respectively. Absorbance and interference data for PA wt and PA wt+LF were also analyzed globally in SEDPHAT 9.4 (Boukari et al., (2004) *Phys Rev Lett* 93(9):098106) in terms of a hybrid continuous c(s) distribution and global discrete species representing the major component. Solution densities ρ were measured at 20.000° C. using an Anton Paar DMA 5000 density meter, solution viscosities η were measured at 20.00° C. on an Anton Paar AMVn rolling ball viscometer, and protein partial specific volumes v were calculated in SEDNTERP 1.09 (Cole et al., (2008) *Methods Cell Biol* 84:143-179) based on the amino acid sequence.

Electrophysiological Measurements

To form solvent-free planar lipid bilayers with the lipid monolayer opposition technique (Montal et al., 1972, Proc. Natl. Acda. Sci. 69:3561-3566), the inventors used a 5 mg/mL stock solution of diphytanoyl phosphatidylcholine (Avanti Polar lipids, Inc., Alabaster, Ala.) in pentane (Burdick and Jackson, Muskegon, Mich.). Bilayer lipid membranes were formed on a 60-μm diameter aperture in the 15-μm-thick Teflon film that separated the two compartments as described in detail before (Kasianowicz and Bezrukov, 1995, Biophys. J. 69:94-105). The 0.1 M aqueous solution of KCl filtered at 0.45 μm (Sigma, St. Louis, Mo.) was buffered at pH 6 (MES, Sigma) at room temperature (23±0.5°) C. $PA_{63}$ channels were formed by adding 1 μL of 13 μg/mL solution of furin-cleaved PA wt, (1-2) μL of 2.37 μg/mL solution of furin-cleaved PA-NS+PA-D512K, or (1-2) μL of 3.17 μg/mL solution of furin-cleaved PA-GN+ PA-D512K to the 1.5 mL aqueous phase on the cis half of the chamber. These concentrations allowed collection of data from up to 100 consecutive single PA63 channel insertions. Under this protocol, channel insertions were always directional as judged by channel conductance asymmetry in the applied transmembrane voltage. The electrical potential difference across the lipid bilayer was applied with a pair of Ag—AgCl electrodes in 2 M KCl, 1.5% agarose (Bethesda Research Laboratory, Gaithersburg, Md.) bridges. Measurements were performed at 50-mV applied voltage. The potential is defined as positive if it is higher on the side of protein addition (cis-side). Conductance measurements were done using an Axopatch 200B amplifier (Axon Instruments, Inc., Foster City, Calif.) in the voltage clamp mode. Signals were filtered by a low-pass 8-pole Butterworth filter (Model 9002, Frequency Devices, Inc., Haverhill, Mass.) at 15 kHz and sampled with a frequency of 50 kHz. Amplitude analysis was performed with ClampFit 10.2 (Molecular Devices) and OriginPro 8.5 (OriginLab) software.

Furin Cleavage and Purification of PA-LF Complexes

Purified PA variants were mixed with furin at a 4000:1 mass ratio of PA:furin in 5 mM Hepes, pH 7.5, 0.2 mM CaCl2, 0.05 mM EDTA, and 0.02% octyl glucoside. Samples were mixed by rocking at 25° C. for 3 h, then placed at 4° C. overnight. Cleaved octameric PA variants were combined in the presence of LF. The octameric complex and wild-type PA alone were then purified using a MonoQ ion exchange column as previously described (Singh et al., 1999, *Infect. Immun.* 67:1853-1859). Fractions containing the desired complex were pooled and concentrated using Amicon Ultra concentrators. Heptameric wild type PA was then mixed with stoichiometric LF.

Native Gel Electrophoresis of PA Oligomers

Electrophoresis of protein complexes was performed as previously described (Singh et al., supra). Acrylamide PhastGel (GE Healthcare) 4-15% gradient gels were soaked for 2 hours at room temperature in 0.112 M acetic acid, 0.112 M Tris, pH 6.4, 2 mg/mL CHAPS then dried prior to use. Buffer strips were soaked in 0.88 M L-alanine, 0.25M Tris, pH 8.8, 2 mg/mL CHAPS until use. Complex samples were prepared in 50 mM CHES, pH 9.0 and 2 mg/mL CHAPS, and were run using the standard native gel electrophoresis program on the PhastGel system. Gels were then stained with Coomassie blue, destained, fixed, and dried.

Dynamic Light Scattering

Homogeneity of protein preparations was assessed by dynamic light scattering (DLS). DLS measurements were made with a 10-mm path length cell at 25° C. using a NanoS Zetasizer (Malvern, Inc.) with a 1 mL sample in a glass cuvette (Malvern, PCS1115) and with a 40-4 sample in a disposable polystyrene cuvette (Malvern, ZEN0040) at concentrations of 0.25, 0.5, and 1.0 mg/mL. For each DLS measurement, samples were centrifuged at 14,000 rpm for 10 min in an Eppendorf 1514C centrifuge then filtered through a 0.2-μm inorganic membrane (Anotop10, Whatman) before dispensing in the measuring cuvette. The DLS measurements were repeated after incubating 1, 2, 6, 12, and 24 h at 25° C. The data were processed with Malvern Zetasizer software using General Purpose and Protein Analysis models.

Results

A library was constructed by partially randomizing several codons in a plasmid encoding PA-D512K. Amino acid substitutions at the positions selected could potentially complement the D512K mutation on an adjacent monomer within the oligomer, restoring the ability to form functional oligomers. Such "gain-of-function" mutations are easier to identify within a library in which all other members are inactive. As it was feasible to survey only a few thousand clones for toxicity, the inventors designed a library that would contain less than 5000 members. It was anticipated that charge reversal mutations were most likely to achieve complementation of the PA-D512K mutation. Examination of the crystal structure of the heptameric oligomer identified four positively-charged residues on the opposite face of PA within 6 Å of the D512K mutation as candidate residues for mutation. The inventors focused on the portion of the codon table that would lead to charge reversal (FIG. 7). By using a degenerate RRM codon (with R=A or G, and M=A or C), seven amino acid residues were accessed using eight different codons: aspartic acid, glutamic acid, lysine, arginine, asparagine, serine, and glycine. This focused library contained a total of 4,096 codons at the DNA level ($8^4$=4,096), coding for 2,401 unique proteins ($7^4$=2,401).

Individual colonies from the library were grown in 96-well plates, and supernatants containing the ectopically-expressed PA variants were mixed with FP59 and placed on RAW264.7 cells to assess toxin function (FP59 is a fusion protein of the N-terminal PA binding domain of LF with the catalytic domain of *Pseudomonas* exotoxin A). After screening 1500 transformants, two gain of function mutants were identified. Each contained substitutions at residues 245 and 252. The locations of these residues relative to residue 512 are shown in FIG. 2. The proteins were purified and characterized in assays containing FP59 (FIG. 3A). In toxicity assays, wild type PA gave an $EC_{50}$ of 2.9 pM, while PA K245G R252N D512K (abbreviated as PA-GNK, $EC_{50}$=5.6 pM) was 1.9-fold less toxic than wild type PA, and PA K245N R252S D512K (abbreviated as PA-NSK, $EC_{50}$=10.3 pM) was 3.5-fold less toxic than wild type PA.

Complementary PA variants were next constructed by removing the D512K point mutation from the coding sequence of the doubly-mutated proteins. PA-D512K and the two PA variants, referred to as PA-GN and PA-NS, were found to be non-toxic at concentrations 1,000-fold greater than the EC$_{50}$ of wild type PA (FIG. 3B). However, combining PA-D512K with either PA-GN or PA-NS generated high toxicity comparable to that of wild type PA, yielding EC$_{50}$ values of 3.9 pM, 9.4 pM, and 12.2 pM for wild type PA, PA-D512K+PA-GN, and PA-D512K+PA-NS, respectively (FIG. 3C). The putative octameric species were not toxic without an effector protein (FIG. 3D). Similar results were obtained by in vivo toxicity studies in mice, where only mixtures of two complementary variants were toxic when administered with either FP59 or LF (FIGS. 3E and F).

Biophysical characterization confirmed that octameric species were formed upon mixing the two complementary PA variants. Preformed heptamer combined with LF and the octamer complex formed in the presence of LF migrated differently by native gel electrophoresis (FIG. 4). Dynamic light scattering measurements of oligomers composed of wild type PA, PA-D512K+PA-GN+LF, and PA-D512K+PA-NS+LF revealed that each sample was monodisperse, so that only one oligomeric species was present per sample (FIG. 8). Sedimentation velocity experiments yielded a sedimentation coefficient distribution [c(s)] profile for wild type PA oligomer indicative of a major species at 15.15±0.01 S (FIG. 5A), corresponding to an estimated molar mass of 520±10 kDa, which is somewhat larger than the expected mass of the PA heptamer ($M_{calc}$=444 kDa). Similarly, sedimentation data for the wild type PA+LF complex indicated the presence of a major species at 17.86±0.08 S, along with what appears to be free PA heptamer. The estimated molar mass of 700±20 kDa is consistent with the expected stoichiometry of 7 $PA_{63}$ units carrying 3 LF molecules ($M_{calc}$=715 kDa). The PA-D512K+PA-GN+LF species gave a sedimentation coefficient of 22.05±0.05 S and an estimated molar mass of 950±30 kDa, whereas the PA-D512K+PA-NS+LF preparation has a sedimentation coefficient of 22.35±0.03 S and an estimated mass of 905±35 kDa, both close to the expected 868 kDa mass of 8 $PA_{63}$ moieties with 4 LF molecules.

Evidence of octameric assembly was obtained by use of electron microscopy (EM) (FIG. 5B) and by electrophysiological measurements (FIG. S3). Specimens negatively stained and imaged by cryo-EM clearly demonstrated heptameric and octameric species in the wild type and complementary variant samples, respectively. Analysis of at least 131 independent, obviously intact and axially oriented oligomers from each sample by reference free alignment revealed that both complementary variants assembled only as octameric species, while wild type PA generated heptameric species (FIG. 5B). Analyses in artificial lipid bilayers confirmed that the complementary pairs of PA variants formed ion-conducting channels that were similar to, but distinguishable from, those produced by wild type PA (FIG. 9).

The requirement that two PA variants combine to produce toxicity offered a strategy to create tumor-targeting agents of increased specificity. In previous work, PA variants were created in which the furin activation sequence was replaced by sequences cleaved by either urokinase plasminogen activator (i.e., PA-U2) (Liu et al., *J. Biol. Chem.* 276, 17976-17984, 2001) or matrix metalloproteases (i.e., PA-L1) (Liu et al., *Cancer Res.* 60, 6061-6067, 2000), two overexpressed by numerous tumors. These variants contained additional mutations so that PA-U2 and PA-L1 monomers had to be adjacent within an oligomer to form native LF binding sites (Liu et al., *Nat. Biotechnol.* 23, 725-730, 2005). However, significant toxicity was still observed for each individual protein, as these mutations did not completely eliminate LF binding in the homo-oligomers. In contrast, introducing the D512K and GN or NS mutations into PA-U2 (PA-U2-D512K) and PA-L1 (PA-L1-GN or PA-L1-NS), respectively, produced a targeting system having an absolute requirement for both proteases to intoxicate a target cell. This result was observed, with a pair of complementary proteins (7.5 μg PA-L1-GN+7.5 μg PA-U2-D512K+7.5 μg LF) completely inhibiting tumor growth, while the individual proteins had no effect, allowing tumors to grow at the same rate as those treated with PBS (FIG. 6A). No toxicity was observed, and there were no decreases in body weight in any experimental condition (FIG. 6A). Comparison of the previous intercomplementing format with the new octameric delivery system in the nude mouse tumor model using A549 cells with a dose of 50 μg of total PA variants with 25 μg LF showed that both systems were equally effective at decreasing tumor size, while much less toxicity was induced by the octameric system (FIG. 6B).

Tissue culture experiments showed that toxicity was effectively eliminated when either protease activity was blocked, as was achieved using Ilomastat (a matrix metalloprotease inhibitor) or Nafamostat mesylate (an inhibitor of serine proteases of the class encompassing urokinase plasminogen activator) (FIG. 10). It was also found that C57BL/6J mice were able to tolerate six doses of 80 μg complementary PA variants (40 μg PA-L1-GN+40 μg PA-U2-D512K) with 40 μg LF (Table 1), while the same dose of the previously-described PA-U2+PA-L1 intercomplementing proteins caused 3 of 5 animals to succumb, thereby establishing an approximate $LD_{50}$ for the intercomplementing system. A doubling of the dose to 80 μg PA-U2-D512K+80 μg PA-L1-GN+80 μg LF resulted in 4 of 7 mice surviving, thereby identifying an approximate $LD_{50}$ for the octameric system. All control animals that received 80 μg of wild type PA with 40 μg LF succumbed after 2 doses. Serum from eight surviving animals in the maximum tolerated dose study revealed that all samples contained normal levels of blood urea nitrogen and creatinine (Table 2). Alanine aminotransferase (ALT) levels were all below 60 U/L (normal range is 17-77 U/L), and all but one animal had aspartate aminotransferase (AST) levels below 120 U/L (normal range is 54-298 U/L). This animal received the highest dose of toxin (160 μg PA-U2-D512K+160 μg PA-L1-GN+160 μg LF) and exhibited an AST level of 317 U/L, which is elevated but still not at levels indicating liver damage.

Electrophysiological measurements of oligomers on lipid bilayer membranes: To determine whether wild type PA, PA-NS+PAD512K, and PA-GN+PA-D512K formed stable ion channels, the inventors reconstituted furin protease activated aliquots of each into lipid bilayer membranes. Typical ion currents through the three variants of the PA63 channels in 0.1 M KCl solutions are presented in FIG. 9A. Although single channel conductances of the amples were similar (FIGS. 9A and B), the average conductances of the octameric channels were higher than those of heptameric ones (FIG. 9C). However, the current-noise characteristics for these channels were comparable. Both the heptameric and octameric forms of $PA_{63}$ possessed vigorous voltage-independent channel flickering between open and completely closed states. This type of 1/f fast flickering was previously reported (Blaustein et al., 1990, *J. Gen. Physiol.* 96:921-942) and recently discussed (Nestorovich et al., 2010, *Biophys. J.* 99:134-143). In FIG. 9A, the 1/f fast flickering was removed to a large extent with a 50-ms filter, but the longest flickering events were clearly seen. In addition, wild type PA, PANS+PA-D512K, and PA-GN+PA-D512K channels exhibited strong voltage-dependent gating of unknown origin, like that observed with many β-barrel channels. The individual PA-NS, PA-GN, and PA-D512K proteins did not show ion channel activity in lipid bilayer membranes even at concentrations 10-fold higher than those used for the mixtures.

TABLE 1

Survival data for maximum tolerated dose study in mice. Mice were injected with toxin intraperitoneally using a six-dose regimen identical to that used in the tumor studies, and they were followed for survival.

| Mouse Strain | Toxin Challenge | # Surviving |
|---|---|---|
| C57BL/6J | 80 µg PA-WT + 40 µg LF | 0/2 |
| C57BL/6J | 40 µg PA-U2-D512K + 40 µg PA-L1-GN + 40 µg LF | 2/2 |
| C57BL/6J | 80 µg PA-U2-D512K + 80 µg PA-L1-GN + 80 µg LF | 4/7 |
| C57BL/6J | 160 µg PA-U2-D512K + 160 µg PA-L1-GN + 160 µg LF | 1/5 |
| C57BL/6J | 40 µg PA-U2-R200A + 40 µg PA-L1-I210A + 40 µg LF | 2/5 |
| C57BL/6J | 80 µg PA-U2-R200A + 80 µg PA-L1-I210A + 80 µg LF | 0/5 |
| Nude | 50 µg PA-U2-D512K + 50 µg PA-L1-GN + 50 µg LF | 2/3 |
| Nude | 75 µg PA-U2-D512K + 75 µg PA-L1-GN + 75 µg LF | 3/3 |

| Mouse Strain | Toxin Challenge | BUN (mg/dL) | Creatinine (mg/dL) | ALT (U/L) | AST (U/L) |
|---|---|---|---|---|---|
| Nude | 50 µg PA-U2-D512K + 50 µg PA-L1-GN + 50 µg LF | 19 | <0.2 | 55 | 74 |
| Nude | 50 µg PA-U2-D512K + 50 µg PA-L1-GN + 50 µg LF | 21 | <0.2 | 55 | 114 |
| Nude | 75 µg PA-U2-D512K + 75 µg PA-L1-GN + 75 µg LF | 20 | <0.2 | 31 | 107 |
| Nude | 75 µg PA-U2-D512K + 75 µg PA-L1-GN + 75 µg LF | 23 | <0.2 | 44 | 98 |
| Nude | 75 µg PA-U2-D512K + 75 µg PA-L1-GN + 75 µg LF | 25 | <0.2 | 39 | 93 |
| C57BL/6J | 80 µg PA-U2-D512K + 80 µg PA-L1-GN + 80 µg LF | 18 | <0.2 | 25 | 70 |
| C57BL/6J | 80 µg PA-U2-D512K + 80 µg PA-L1-GN + 80 µg LF | 23 | <0.2 | 27 | 61 |
| C57BL/6J | 160 µg PA-U2-D512K + 160 µg PA-L1-GN + 160 µg LF | 18 | <0.2 | 55 | 317 |
| | Normal range | 8-33 | 0.2-0.9 | 17-77 | 54-298 |

Discussion

In this work, the present inventors successfully engineered PA so that two complementary versions of PA are required to produce a functional octamer. These octamers were characterized by several biophysical techniques and shown that they possess near-wild type toxicity in vitro and in vivo when in combination, but are nontoxic individually. Additionally, the inventors applied this system to require that two proteases act separately to activate a functional toxin complex. The protease-activated protein mixture completely halted tumor growth in a mouse model, while individual components had no observable toxicity. In principle, the mutagenesis and screening process described here can be repeated to create an octamer containing up to eight distinct specificity requirements for cell targeting. These steps could use some of the seven PA residues in addition to D512 that were previously shown to prevent oligomerization when mutated to alanine (Mogridge et al., (2001) *J Bacteriol* 183(6):2111-2116; Ahuja et al., (2001) *Biochem Biophys Res Commun* 287(2):542-549).

As mentioned earlier, the earlier expectation was that negatively-charged amino acids would be selected to complement the charge reversal at position D512K. Instead, the screen produced complementary mutations where positively-charged residues were replaced by small uncharged amino acids, e.g., K245G, K245N, R252N, and R252S. This result showed that shape complementarity to accommodate the lysine mutation (D512K) was the most important factor, as all selected amino acids (Gly, Asn, and Ser) were considerably smaller than the lysines or arginines that they replaced. The library created and screened in this work was relatively small, and it is quite possible that screening of a larger, more diverse library would identify other mutant proteins having properties like those of PA-GN and PA-NS.

Pore forming toxins are often homooligomeric, with the prototypical example being staphylococcal α-hemolysin (α-HL), a β-barrel pore-forming toxin (Song et al. (1996) *Science* 274(5294):1859-1866). The staphylococcal α-HL has been shown to form heptamers, but under certain conditions will also form hexameric rings (Czajkowsky et al., (1998) *J Mol Biol* 276(2):325-330). Anthrax toxin was long thought to form heptamers exclusively (Milne et al. (1994) *J Biol Chem* 269(32):20607-20612), but the work by Krantz and colleagues has shown that functional octamers can also be formed (Kintzer et al. (2009) *J Mol Biol* 392:614-629; Feld et al., (2011) *J Mol Biol* 415(1):159-174; Kintzer et al., (2010) *PLoS ONE* 5(11):e13888; Feld et al. (2010) *Nat Struct Mol Biol* 17(11):1383-1391), a conclusion confirmed and extended by these studies. This suggests a cautionary approach when considering the oligomeric states of other anthrax-like toxins, such as clostridial C2 toxin and iota toxin (Barth et al., (2004) *Microbiol Mol Biol Rev* 68(3): 373-402), and even all other pore forming toxins, to include consideration that alternative oligomeric forms might be present in certain situations.

One can envision using complementary PA variants like those described here as a platform to create "nano-toolboxes" for assembling several different proteins or enzymatic activities together in reproducible combinations to perform processes on the nanoscale. Also, these PA variants can be used to understand the specific receptor signaling requirements for uptake of anthrax toxin. Overall, this work provides the possibility of development and use of oligomers in targeting applications as presented here and enhances our understanding of toxin function and toxin-host interactions.

All patents, patent applications, and other publications, including GenBank Accession Numbers, cited in this application are incorporated by reference in the entirety for all purposes.

What is claimed is:

1. A method of targeted delivery of a compound to a cell overexpressing a first proteinase and a second proteinase that are different from each other, the method comprising the steps of:
   (a) administering to the cell (1) a first mutant protective antigen protein that comprises a cleavage site recognized by the first proteinase in place of the native protective antigen furin-recognized cleavage site and is cleavable by the first proteinase; and (2) a second mutant protective antigen protein that comprises a cleavage site recognized by the second proteinase in place of the native protective antigen furin-recognized cleavage site and is cleavable by the second proteinase, wherein the first mutant protective antigen protein further comprises a mutation at a position corresponding to residue 512 of wild-type Bacillus anthracis protective antigen protein, and the second mutant protective antigen protein further comprises a mutation at a position corresponding to residue 245 of wild-type Bacillus anthracis protective antigen protein and a mutation at a position corresponding to residue 252 of wild-type Bacillus anthracis protective antigen protein, and wherein after cleavage by the first and second proteinases the first and second mutant protective antigen proteins form a hetero-oligomer but do not form a homo-oligomer; and
   (b) administering to the cell a compound comprising a protective antigen binding site, wherein the compound comprises a lethal factor polypeptide comprising at least a portion of the native lethal factor protein and binds to the hetero-oligomer and is translocated into the cell.

2. The method of claim 1, wherein the first proteinase is a plasminogen activator and the second proteinase is a matrix metalloproteinase, or vice versa.

3. The method of claim 1, wherein the first or the second proteinase is furin.

4. The method of claim 3, wherein the native protective antigen furin-recognized cleavage site in the first or second mutant protective antigen protein that is cleavable by furin is replaced with RAAR (SEQ ID NO:16) or RARAAR (SEQ ID NO:17).

5. The method of claim 1, wherein the cell is a cancer cell.

6. The method of claim 5, wherein the cell is within a human body.

7. The method of claim 2, wherein the plasminogen activator is tissue plasminogen activator (t-PA) or urokinase plasminogen activator (u-PA).

8. The method of claim 2, wherein the matrix metalloproteinase is MMP-2 (gelatinase A), MMP-9 (gelatinase B), or membrane-type 1 MMP (MT1-MMP).

9. The method of claim 1, wherein the compound is a lethal factor polypeptide comprising at least a portion of the native lethal factor protein.

10. The method of claim 9, wherein the lethal factor polypeptide is the native lethal factor protein.

11. The method of claim 9, wherein the lethal factor polypeptide is the 1-254 segment of the native lethal factor protein.

12. The method of claim 9, wherein the lethal factor polypeptide is the native lethal factor or a portion thereof fused to a heterologous molecule.

13. The method of claim 12, wherein the heterologous molecule is shiga toxin, A chain of diphtheria toxin, or Pseudomonas exotoxin A.

14. The method of claim 12, wherein the heterologous molecule is a detectable moiety.

15. The method of claim 12, wherein the heterologous molecule is a nucleic acid.

16. The method of claim 12, wherein the heterologous molecule is covalently linked to the native lethal factor or a portion thereof.

17. The method of claim 1, wherein the compound is a recombinant polypeptide.

18. The method of claim 1, wherein the compound is FP59.

19. The method of claim 6, wherein the first and second mutant protective antigen proteins and the compound are administered systemically to the human.

20. The method of claim 2, wherein the matrix metalloproteinase-recognized cleavage site is GPLGMLSQ (SEQ ID NO:9) or GPLGLWAQ (SEQ ID NO:10).

21. The method of claim 2, wherein the plasminogen activator-recognized cleavage site is PCPGRVVGG (SEQ ID NO:11), PGSGRSA (SEQ ID NO:12), PGSGKSA (SEQ ID NO:13), or PQRGRSA (SEQ ID NO:14).

22. The method of claim 1, wherein the hetero-oligomer is an octamer consisting of four of each of the first and second mutant protective antigen proteins.

23. The method of claim 1, wherein residue 512 is substituted by Lys, and residue 245 is substituted by Gly and residue 252 is substituted by Asn.

24. The method of claim 1, wherein residue 512 is substituted by Lys, and residue 245 is substituted by Asn and residue 252 is substituted by Ser.

25. The method of claim 23 or 24, wherein the first proteinase is u-PA and the second proteinase is MMP-2, and wherein the compound is the native lethal factor protein.

26. A kit for targeted delivery of a compound to a cell overexpressing a first proteinase and a second proteinase that are different from each other, the kit comprising:
   (1) a first mutant protective antigen protein that comprises a cleavage site recognized by the first proteinase in place of the native protective antigen furin-recognized cleavage site and is cleavable by the first proteinase;
   (2) a second mutant protective antigen protein that comprises cleavage site recognized by the second proteinase in place of the native protective antigen furin-recognized cleavage site and is cleavable by the second proteinase; and
   (3) a compound comprising a protective antigen binding site,
   wherein the first mutant protective antigen protein further comprises a mutation at a position corresponding to residue 512 of wild-type Bacillus anthracis protective antigen protein, and the second mutant protective antigen protein further comprises a mutation at a position corresponding to residue 245 of wild-type Bacillus anthracis protective antigen protein and a mutation at a position corresponding to residue 252 of wild-type Bacillus anthracis protective antigen protein, wherein after cleavage by the first and second proteinases the first and second mutant protective antigen proteins form a hetero-oligomer but do not form a homo-oligomer, and wherein the compound comprises a lethal factor polypeptide comprising at least a portion of the native lethal factor protein and binds to the hetero-oligomer and is translocated into the target cell.

27. The kit of claim 26, wherein the first proteinase is a plasminogen activator and the second proteinase is a matrix metalloproteinase, or vice versa.

28. The kit of claim 26, wherein the first or the second proteinase is furin.

29. The kit of claim 27, wherein the plasminogen activator is tissue plasminogen activator (t-PA) or urokinase plasminogen activator (u-PA).

30. The kit of claim 27, wherein the matrix metalloproteinase is MMP-2 (gelatinase A), MMP-9 (gelatinase B), or membrane-type 1 MMP (MT1-MMP).

31. The kit of claim 26, wherein the compound is the native lethal factor protein or FP59.

32. The kit of claim 26, wherein residue 512 is substituted by Lys, and residue 245 is substituted by Gly and residue 252 is substituted by Asn.

33. The kit of claim 26, wherein residue 512 is substituted by Lys, and residue 245 is substituted by Asn and residue 252 is substituted by Ser.

34. The kit of claim 29 or 30, wherein the first proteinase is u-PA and the second proteinase is MMP-2, and wherein the compound is the native lethal factor protein.

* * * * *

SEQUENCE LISTING

<160> NUMBER OF SEQ ID NOS: 17

<210> SEQ ID NO 1
<211> LENGTH: 43
<212> TYPE: DNA
<213> ORGANISM: Artificial Sequence
<220> FEATURE:
<223> OTHER INFORMATION: synthetic primer used for site-directed
      mutagenesis reversion of D512K point mutation to wild type

<400> SEQUENCE: 1
ggatagcggc ggttaatcct agtgatccat tagaaacgac taa             43

<210> SEQ ID NO 2
<211> LENGTH: 43
<212> TYPE: DNA
<213> ORGANISM: Artificial Sequence
<220> FEATURE:
<223> OTHER INFORMATION: synthetic sequence used construction of
      PA-U2-D512K with pYS5-PA-U2

<400> SEQUENCE: 2
ggatagcggc ggttaatcct agtaagccat tagaaacgac taa             43

<210> SEQ ID NO 3
<211> LENGTH: 53
<212> TYPE: DNA
<213> ORGANISM: Artificial Sequence
<220> FEATURE:
<223> OTHER INFORMATION: synthetic sequence used construction of
      PA-L1-GN with pYS5-PA-L1

<400> SEQUENCE: 3
ggttacagga cggattgatg gaaatgtatc accagaggca aaccacccce ttg   53

<210> SEQ ID NO 4
<211> LENGTH: 53
<212> TYPE: DNA
<213> ORGANISM: Artificial Sequence
<220> FEATURE:
<223> OTHER INFORMATION: synthetic sequence used construction of
      PA-L1-NS with pYS5-PA-L1

<400> SEQUENCE: 4
ggttacagga cggattgata acaatgtatc accagaggca agccaccccc ttg   53

<210> SEQ ID NO 5
<211> LENGTH: 88
<212> TYPE: DNA
<213> ORGANISM: Artificial Sequence
<220> FEATURE:
<223> OTHER INFORMATION: synthetic overlap extension PCR forward inner
      primer

<400> SEQUENCE: 5
cttctgatcc gtacagtgat ttcgaarrmg ttacaggarr mattgatrrm aatgtatcac   60
cagaggcarr mcacccccett gtggcagc                              88

<210> SEQ ID NO 6
<211> LENGTH: 26
<212> TYPE: DNA
<213> ORGANISM: Artificial Sequence
<220> FEATURE:
<223> OTHER INFORMATION: synthetic overlap extension PCR reverse inner
      primer

<400> SEQUENCE: 6

```
ttcgaaatca ctgtacggat cagaag                                          26
```

<210> SEQ ID NO 7
<211> LENGTH: 23
<212> TYPE: DNA
<213> ORGANISM: Artificial Sequence
<220> FEATURE:
<223> OTHER INFORMATION: synthetic primary and secondary amplification
      forward outer primer

<400> SEQUENCE: 7

```
gacgagcgct tcggtcttaa ctg                                             23
```

<210> SEQ ID NO 8
<211> LENGTH: 24
<212> TYPE: DNA
<213> ORGANISM: Artificial Sequence
<220> FEATURE:
<223> OTHER INFORMATION: synthetic primary and secondary amplification
      reverse outer primer

<400> SEQUENCE: 8

```
agcagccaac tcagcttcct ttcg                                            24
```

<210> SEQ ID NO 9
<211> LENGTH: 8
<212> TYPE: PRT
<213> ORGANISM: Artificial Sequence
<220> FEATURE:
<223> OTHER INFORMATION: synthetic matrix metalloproteinase (MMP)
      recognized cleavage site

<400> SEQUENCE: 9

Gly Pro Leu Gly Met Leu Ser Gln
 1               5

<210> SEQ ID NO 10
<211> LENGTH: 8
<212> TYPE: PRT
<213> ORGANISM: Artificial Sequence
<220> FEATURE:
<223> OTHER INFORMATION: synthetic matrix metalloproteinase (MMP)
      recognized cleavage site

<400> SEQUENCE: 10

Gly Pro Leu Gly Leu Trp Ala Gln
 1               5

<210> SEQ ID NO 11
<211> LENGTH: 9
<212> TYPE: PRT
<213> ORGANISM: Artificial Sequence
<220> FEATURE:
<223> OTHER INFORMATION: synthetic plasminogen activator recognized
      cleavage site

<400> SEQUENCE: 11

Pro Cys Pro Gly Arg Val Val Gly Gly
 1               5

<210> SEQ ID NO 12
<211> LENGTH: 7
<212> TYPE: PRT
<213> ORGANISM: Artificial Sequence
<220> FEATURE:
<223> OTHER INFORMATION: synthetic plasminogen activator recognized
      cleavage site -continued

```
<400> SEQUENCE: 12

Pro Gly Ser Gly Arg Ser Ala
 1               5

<210> SEQ ID NO 13
<211> LENGTH: 7
<212> TYPE: PRT
<213> ORGANISM: Artificial Sequence
<220> FEATURE:
<223> OTHER INFORMATION: synthetic plasminogen activator recognized
      cleavage site

<400> SEQUENCE: 13

Pro Gly Ser Gly Lys Ser Ala
 1               5

<210> SEQ ID NO 14
<211> LENGTH: 7
<212> TYPE: PRT
<213> ORGANISM: Artificial Sequence
<220> FEATURE:
<223> OTHER INFORMATION: synthetic plasminogen activator recognized
      cleavage site

<400> SEQUENCE: 14

Pro Gln Arg Gly Arg Ser Ala
 1               5

<210> SEQ ID NO 15
<211> LENGTH: 4
<212> TYPE: PRT
<213> ORGANISM: Artificial Sequence
<220> FEATURE:
<223> OTHER INFORMATION: synthetic native protective antigen (PA)
      furin-recognized cleavage site

<400> SEQUENCE: 15

Arg Lys Lys Arg
 1

<210> SEQ ID NO 16
<211> LENGTH: 4
<212> TYPE: PRT
<213> ORGANISM: Artificial Sequence
<220> FEATURE:
<223> OTHER INFORMATION: synthetic protective antigen (PA)
      furin-recognized cleavage site replacement mutant

<400> SEQUENCE: 16

Arg Ala Ala Arg
 1

<210> SEQ ID NO 17
<211> LENGTH: 6
<212> TYPE: PRT
<213> ORGANISM: Artificial Sequence
<220> FEATURE:
<223> OTHER INFORMATION: synthetic protective antigen (PA)
      furin-recognized cleavage site replacement mutant

<400> SEQUENCE: 17

Arg Ala Arg Ala Ala Arg
 1               5
```